(12) United States Patent
Hoyes et al.

(10) Patent No.: US 8,283,628 B2
(45) Date of Patent: Oct. 9, 2012

(54) ION MOBILITY SPECTROMETER

(75) Inventors: John Brian Hoyes, Stockport (GB); David J. Langridge, Manchester (GB)

(73) Assignee: Micromass UK Limited, Manchester (GB)

(*) Notice: Subject to any disclaimer, the term of this patent is extended or adjusted under 35 U.S.C. 154(b) by 0 days.

(21) Appl. No.: 13/060,100

(22) PCT Filed: Aug. 14, 2009

(86) PCT No.: PCT/GB2009/002001
§ 371 (c)(1), (2), (4) Date: May 5, 2011

(87) PCT Pub. No.: WO2010/020763
PCT Pub. Date: Feb. 25, 2010

(65) Prior Publication Data
US 2011/0291001 A1    Dec. 1, 2011

Related U.S. Application Data

(60) Provisional application No. 61/093,474, filed on Sep. 2, 2008.

(30) Foreign Application Priority Data

Aug. 22, 2008    (GB) .................................. 0815397.5

(51) Int. Cl.
B01D 59/44    (2006.01)

(52) U.S. Cl. ........ 250/282; 250/281; 250/290; 250/291; 250/292; 250/293

(58) Field of Classification Search .................. 250/281, 250/282, 288, 290–293
See application file for complete search history.

(56) References Cited

U.S. PATENT DOCUMENTS

| | | | |
|---|---|---|---|
| 6,906,319 B2 * | 6/2005 | Hoyes | .................. 250/282 |
| 6,914,241 B2 | 7/2005 | Giles et al. | |
| 2004/0094702 A1 | 5/2004 | Clemmer | |

FOREIGN PATENT DOCUMENTS

| | | |
|---|---|---|
| GB | 2457769 | 9/2009 |
| WO | 2007054712 | 5/2007 |

* cited by examiner

*Primary Examiner* — Michael Maskell
(74) *Attorney, Agent, or Firm* — Diederiks & Whitelaw PLC

(57) ABSTRACT

An ion mobility spectrometer is disclosed wherein ions are passed through an ion mobility spectrometer (5) and become temporally separated. Ions having a relatively high ion mobility are transmitted by a non-destructive ion gate (6) but ions having a relatively low ion mobility are subsequently trapped within the ion mobility spectrometer (5) when the ion gate (6) is switched so as to prevent ions from being onwardly transmitted. Ions which are transmitted by the ion gate (6) are trapped in a downstream ion trap (7). The ions are then returned back upstream to a second upstream ion trap (4).

15 Claims, 23 Drawing Sheets

ION MOBILITY SPECTROMETER

CROSS REFERENCE TO RELATED APPLICATIONS

This application is the National Stage of International Application No. PCT/GB09/002001, filed Aug. 14, 2009 and designating the United States, which claims benefit of and priority to Provisional Patent Application No. 61/093,474, filed Sep. 2, 2008 and United Kingdom Patent Application No. 0815397.5 filed 22 Aug. 2008. The entire contents of these applications are incorporated herein by reference.

The present invention relates to an ion mobility spectrometer or separator, a mass spectrometer, a method of ion mobility separation and a method of mass spectrometry.

The analytical utility of providing a forward impetus for ions confined by RF fields in the presence of gaseous media has long been understood. Particular applications include the creation of collision cells for tandem mass spectrometers wherein fast transit times are desirable e.g. when performing MRM, parent ion scanning or neutral loss experiments on triple quadrupole instruments. Such devices may also be used to separate ions according to their ion mobility and these are finding wider use in hybrid ion mobility-mass spectrometer instruments. Typical pressure ranges of operation are in the region of 0.001 to 10 mbar. There are a number of ways in which the forward impetus can be derived. Some of these ways are briefly described below.

U.S. Pat. No. 6,914,241 (Giles) describes how ions may be separated according to their ion mobility by progressively applying transient DC voltages along the length of an RF ion guide or ion mobility separator comprising a plurality of electrodes. The ion mobility separator may comprise an AC or RF ion guide such as a multipole rod set or a stacked ring set. The ion guide is segmented in the axial direction so that independent transient DC potentials can be applied to each segment. The transient DC potentials are superimposed on top of an AC or RF voltage (which acts to radially confine ions) and/or any constant DC offset voltage. The transient DC potentials generate a travelling wave which moves along the axial direction and translates ions along the ion mobility separator.

A known ion mobility separation device comprises a drift tube comprising a series of rings wherein a constant potential difference is maintained between adjacent members such that a constant electric field is produced. A pulse of ions is introduced into the drift tube which contains a buffer gas and ions separate along the longitudinal axis according to their ion mobility. These devices are operable at atmospheric pressure without RF confinement and can offer resolutions up to 150 (Wu et. A. Anal. Chem. 1988, 70, 4929-4938). Operation at lower pressures more suitable for hybrid ion mobility-mass spectrometer instruments leads to greater diffusion losses and lower resolution. An RF pseudo-potential well may be arranged to confine ions radially and may be used to transport ions efficiently by acting as an ion guide and so solving the problem of diffusion losses. Ions may be propelled along the guide and ions may be separated according to their ion mobility. However, the problem of the lower pressure of operation of mobility separation is that in order to achieve a high resolution of mobility separation, a relatively long drift tube must be employed in order to keep within the low field limit as described in more detail below.

In order to separate ions according to their mobility in an RF ion guide a DC electric field must be generated which is orthogonal to the RF radial confinement. If a constant electric field E is applied to drive the ions through the ion guide containing a gas then the ion will acquire a characteristic velocity:

$$v_d = E \cdot K \quad (1)$$

wherein K is the ion mobility.

To achieve a mobility separation whereby the ions acquire negligible energy compared to the background thermal energy of a gas it is necessary to consider the parameter E/P, wherein P is the pressure of the neutral gas.

To maintain mobility separation in the so called low field regime whereby ions do not receive kinetic energy from the driving field it is required that the parameter E/P is less than about 2V/cm-mbar.

Under low field conditions in a drift tube of length L and applied voltage drop V the resolution is found to be independent of ion mobility and only dependent on the voltage drop such that in the absence of space charge effects:

$$\frac{L}{|\bar{x}|} = \frac{\sqrt{V}}{0.173} \quad (2)$$

wherein $|\bar{x}|$ is the mean displacement of the centre of mass of the moving ion cloud:

The parameter $$\frac{L}{|\bar{x}|}$$

is effectively the resolution of the mobility separation so it can be seen that the performance of the spectrometer can be increased by maintaining larger voltage drops across the drift tube. In hybrid ion mobility-mass spectrometer instruments the typical pressure of the ion mobility drift region is 0.5-1 mbar. Operating at pressures much greater than this puts great demands upon the vacuum system which needs to be differentially pumped in order for the mass spectrometer stages to operate efficiently.

At a typical drift tube length of 20 cm and operating pressure of 0.5 mbar the maximum voltage that can be applied within the low field limit is 20 V giving a maximum resolution of 26. To achieve a resolution of 100 under the same conditions would require a drift tube length of over 3 meters which is impractical for commercial instruments.

It is desired to provide an improved method of ion mobility separation and apparatus for separating ions.

According to an aspect of the present invention there is provided a method of mass spectrometry comprising:

passing a first group of ions through an ion mobility spectrometer or separator in order to separate temporally at least some of the ions;

operating an ion gate so that ions having drift times within a time window T1 are transmitted by the ion gate but ions having drift times outside of the time window T1 are not transmitted by the ion gate; and passing at least some of the ions having drift times within the time window T1 through the ion mobility spectrometer or separator again in order to separate temporally at least some of the ions.

According to the preferred embodiment of the present invention the ion gate preferably comprises an electrode to which a DC and/or RF potential is applied in order to prevent ions from being onwardly transmitted past the ion gate. The ion gate may comprise a discrete electrode arranged upstream of a downstream ion trap. Less preferred embodiments are contemplated wherein the ion gate may comprise an electrode of the downstream ion trap.

The method preferably further comprises:

passing at least some or substantially all of the ions having drift times outside of the time window T1 back through the ion mobility spectrometer or separator and storing the ions in a first upstream ion trap.

According to the preferred embodiment, prior to passing at least some of the ions having drift times within the time window T1 through the ion mobility spectrometer or separator again the method further comprises the steps of: trapping the ions having drift times within the time window T1 in a downstream ion trap, passing the ions back upstream through the ion mobility spectrometer or separator, storing the ions in a second upstream ion trap and ejecting the ions from the second upstream ion trap into the ion mobility spectrometer or separator.

The method preferably further comprises:

operating the ion gate so that ions having drift times within a time window T2 are transmitted by the ion gate but ions having drift times outside of the time window T2 are not transmitted by the ion gate;

passing at least some or substantially all of the ions having drift times outside of the time window T2 back through the ion mobility spectrometer or separator and storing the ions in a first upstream ion trap; and trapping the ions having drift times within the time window T2 in a downstream ion trap, passing the ions back upstream through the ion mobility spectrometer or separator, storing the ions in a second upstream ion trap, ejecting the ions from the second upstream ion trap into the ion mobility spectrometer or separator and passing at least some of the ions having drift times within the time window T2 through the ion mobility spectrometer or separator again in order to separate temporally at least some of the ions.

The method preferably further comprises:

operating the ion gate so that ions having drift times within a time window T3 are transmitted by the ion gate but ions having drift times outside of the time window T3 are not transmitted by the ion gate;

passing at least some or substantially all of the ions having drift times outside of the time window T3 back through the ion mobility spectrometer or separator and storing the ions in a first upstream ion trap; and trapping the ions having drift times within the time window T3 in a downstream ion trap, passing the ions back upstream through the ion mobility spectrometer or separator, storing the ions in a second upstream ion trap, ejecting the ions from the second upstream ion trap into the ion mobility spectrometer or separator and passing at least some of the ions having drift times within the time window T3 through the ion mobility spectrometer or separator again in order to separate temporally at least some of the ions.

According to the preferred embodiment the above process may be further repeated so that ions are gated further times by the ion gate. Ions having drift times within the drift time window or sampling window determined by the ion gate are returned to the second upstream ion trap whilst ions which do not pass through the ion gate are temporarily stored in the first upstream ion trap. After ions have been passed through the ion mobility spectrometer or separator a desired number of times and gated by the ion gate, the ions are then passed through the ion mobility spectrometer or separator and a conventional ion mobility scan is performed.

According to the preferred embodiment the method further comprises mass analysing at least some of the ions which emerge from the ion mobility spectrometer or separator after ions have been passed multiple times through the ion mobility spectrometer or separator.

The first time window T1 and/or the second time window T2 and/or the third time window T3 are preferably substantially the same or less preferably substantially different.

The method preferably further comprises:

ejecting at least some of the ions having drift times outside of the time windows T1, T2 and T3 from the first upstream ion trap into the ion mobility spectrometer or separator as a second group of ions.

According to the preferred embodiment the method further comprises passing the second group of ions through the ion mobility spectrometer or separator in order to separate temporally at least some of the ions;

operating an ion gate so that ions having drift times within a time window T4 are transmitted by the ion gate but ions having drift times outside of the time window T4 are not transmitted by the ion gate; and passing at least some of the ions having drift times within the time window T4 through the ion mobility spectrometer or separator again in order to separate temporally at least some of the ions.

According to the preferred embodiment the method further comprises:

passing at least some or substantially all of the ions having drift times outside of the time window T4 back through the ion mobility spectrometer or separator and storing the ions in a first upstream ion trap.

According to the preferred embodiment prior to passing at least some of the ions having drift times within the time window T4 through the ion mobility spectrometer or separator again the method further comprises the steps of:

trapping the ions having drift times within the time window T4 in a downstream ion trap, passing the ions back upstream through the ion mobility spectrometer or separator, storing the ions in a second upstream ion trap and ejecting the ions from the second upstream ion trap into the ion mobility spectrometer or separator.

According to the preferred embodiment the method further comprises:

operating the ion gate so that ions having drift times within a time window T5 are transmitted by the ion gate but ions having drift times outside of the time window T5 are not transmitted by the ion gate;

passing at least some or substantially all of the ions having drift times outside of the time window T5 back through the ion mobility spectrometer or separator and storing the ions in a first upstream ion trap; and trapping the ions having drift times within the time window T5 in a downstream ion trap, passing the ions back upstream through the ion mobility spectrometer or separator, storing the ions in a second upstream ion trap, ejecting the ions from the second upstream ion trap into the ion mobility spectrometer or separator and passing at least some of the ions having drift times within the time window T5 through the ion mobility spectrometer or separator again in order to separate temporally at least some of the ions.

According to the preferred embodiment the method further comprises:

operating the ion gate so that ions having drift times within a time window T6 are transmitted by the ion gate but ions having drift times outside of the time window T6 are not transmitted by the ion gate;

passing at least some or substantially all of the ions having drift times outside of the time window T6 back through the ion mobility spectrometer or separator and storing the ions in a first upstream ion trap; and trapping the ions having drift times within the time window T6 in a downstream ion trap, passing the ions back upstream through the ion mobility spectrometer or separator, storing the ions in a second upstream ion trap, ejecting the ions from the second upstream ion trap into the ion mobility spectrometer or separator and passing at least some of the ions having drift times within the time window T6 through the ion mobility spectrometer or separator again in order to separate temporally at least some of the ions.

According to the preferred embodiment the above process may be further repeated so that ions are gated further times by the ion gate. Ions having drift times within the drift time window or sampling window determined by the ion gate are returned to the second upstream ion trap whilst ions which do not pass through the ion gate are temporarily stored in the first upstream ion trap. After ions have been passed through the ion mobility spectrometer or separator a desired number of times and gated by the ion gate, the ions are then passed through the ion mobility spectrometer or separator and a conventional ion mobility scan is performed.

The method preferably further comprises mass analysing at least some of the ions which emerge from the ion mobility spectrometer or separator after ions have been passed multiple times through the ion mobility spectrometer or separator.

According to an embodiment either:

(i) the time window T4 and/or the time window T5 and/or the time window T6 are substantially the same; or (ii) the time window T4 and/or the time window T5 and/or the time window T6 are substantially different.

According to an embodiment either:

(i) the time window T4 and/or the time window T5 and/or the time window T6 are substantially different to the time window T1 and/or the time window T2 and/or the time window T3; or (ii) the time window T4 and/or the time window T5 and/or the time window T6 are substantially the same as the time window T1 and/or the time window T2 and/or the time window T3.

According to an embodiment the time window T1 preferably encompasses ions having drift times in the range $T1_{min}$-$T1_{max}$. According to an embodiment the time window T2 preferably encompasses ions having drift times in the range $T2_{min}$-$T2_{max}$. According to an embodiment the time window T3 preferably encompasses ions having drift times in the range $T3_{min}$-$T3_{max}$. According to an embodiment the time window T4 preferably encompasses ions having drift times in the range $T4_{min}$-$T4_{max}$. According to an embodiment the time window T5 preferably encompasses ions having drift times in the range $T5_{min}$-$T5_{max}$. According to an embodiment the time window T6 preferably encompasses ions having drift times in the range $T6_{min}$-$T6_{max}$.

According to a first embodiment $T1_{min}=T2_{min}=T3_{min}$. Preferably, $T1_{max}=T2_{max}=T3_{max}$. Preferably, $T4_{min}=T6_{min}=T6_{min}$. Preferably, $T4_{max}=T5_{max}=T6_{max}$. Preferably, either $T4_{min}=T1_{max}$ or $T1_{min}=T4_{max}$.

According to a second embodiment $T1_{min}=T2_{min}=T3_{min}$. Preferably, $T1_{max}=T2_{max}=T3_{max}$. Preferably, $T4_{min}=T6_{min}=T6_{min}$. Preferably, $T4_{max}=T5_{max}=T6_{max}$. Preferably, $T4_{max}>T1_{max}$.

The method preferably further comprises obtaining an ion mobility spectrum corresponding substantially to a single ion species by:

determining the mean drift time of ions through the ion mobility spectrometer or separator as a function of the maximum drift time of ions transmitted by the ion gate;

determining at least one time period during which the mean drift time remains substantially constant as a function of the maximum drift time of ions transmitted by the ion gate; and forming a composite ion mobility spectrum by summing ion mobility data obtained during the time period.

The ions having drift times within the time window T1 and/or the time window T2 and/or the time window T3 and/or the time window T4 and/or the time window T5 and/or the time window T6 are preferably not substantially fragmented when entering and whilst being stored in the downstream ion trap and/or when entering and whilst being stored in the second upstream ion trap.

According to the preferred embodiment ions having drift times outside the time window T1 and/or outside the time window T2 and/or outside the time window T3 and/or outside the time window T4 and/or outside the time window T5 and/or outside the time window T6 are not substantially fragmented when entering and whilst being stored in the first upstream ion trap.

According to an aspect of the present invention there is provided a mass spectrometer comprising:

an ion mobility spectrometer or separator;

an ion gate arranged downstream of the ion mobility spectrometer or separator; and a control system arranged and adapted:

(i) to cause a first group of ions to pass through the ion mobility spectrometer or separator in order to separate temporally at least some ions;

(ii) to operate the ion gate so that ions having drift times within a time window T1 are transmitted by the ion gate but ions having drift times outside of the time window T1 are not transmitted by the ion gate; and (iii) to cause at least some of the ions having drift times within the time window T1 to pass through the ion mobility spectrometer or separator again in order to separate temporally at least some of the ions.

According to an aspect of the present invention there is provided a method of mass spectrometry comprising:

(i) passing ions through an ion mobility spectrometer or separator in order to separate temporally the ions and applying a first time window and a second time window to ions emerging from the ion mobility spectrometer or separator;

(ii) passing ions having drift times through the ion mobility spectrometer or separator falling within the first time window through the ion mobility spectrometer or separator again in order to separate temporally the ions and again applying the first time window and the second time window to ions emerging from the ion mobility spectrometer or separator;

(iii) storing any ions having drift times through the ion mobility spectrometer or separator falling within the second time window in an ion trap;

(iv) repeating steps (ii) and (iii) one or more times; and then (v) ejecting ions stored in the ion trap and passing the ions through the ion mobility spectrometer or separator in order to separate temporally the ions and applying the first time window and the second time window to ions emerging from the ion mobility spectrometer or separator;

(vi) passing ions having drift times through the ion mobility spectrometer or separator falling within the second time window through the ion mobility spectrometer or separator again in order to separate temporally the ions and again applying the first time window and the second time window to ions emerging from the ion mobility spectrometer or separator; and (vii) repeating step (vi) one or more times.

According to an embodiment the first time window encompasses ions having drift times in the range $T1_{min}$-$T1_{max}$ and the second time window encompasses ions having drift times $>T1_{max}$ or $<T1_{min}$.

According to an aspect of the present invention there is provided a mass spectrometer comprising:

an ion mobility spectrometer or separator;

an ion gate arranged downstream of the ion mobility spectrometer or separator; and a control system arranged and adapted:

(i) to cause ions to pass through an ion mobility spectrometer or separator in order to separate temporally the ions and to apply a first time window and a second time window to ions emerging from the ion mobility spectrometer or separator;

(ii) to cause ions having drift times through the ion mobility spectrometer or separator falling within the first time window to pass through the ion mobility spectrometer or separator again in order to separate temporally the ions and again to apply the first time window and the second time window to ions emerging from the ion mobility spectrometer or separator;

(iii) to cause any ions having drift times through the ion mobility spectrometer or separator falling within the second time window to be stored an ion trap;

(iv) to repeat steps (ii) and (iii) one or more times; and then (v) to eject ions stored in the ion trap and to cause the ions to pass through the ion mobility spectrometer or separator in order to separate temporally the ions and to apply the first time window and the second time window to ions emerging from the ion mobility spectrometer or separator;

(vi) to cause ions having drift times through the ion mobility spectrometer or separator falling within the second time window to pass through ion mobility spectrometer or separator again in order to separate temporally the ions and again to apply the first time window and the second time window to ions emerging from the ion mobility spectrometer or separator; and (vii) to repeat step (vi) one or more times.

According to aspect of the present invention there is provided a method of mass spectrometry comprising:

(i) passing ions through an ion mobility spectrometer or separator in order to separate temporally the ions and applying a first time window and a second time window to ions emerging from the ion mobility spectrometer or separator;

(ii) passing ions having drift times through the ion mobility spectrometer or separator falling within the first time window through the ion mobility spectrometer or separator again in order to separate temporally the ions and again applying the first time window and the second time window to ions emerging from the ion mobility spectrometer or separator;

(iii) storing any ions having drift times through the ion mobility spectrometer or separator falling within the second time window in an ion trap;

(iv) repeating steps (ii) and (iii) one or more times; and then (v) ejecting ions stored in the ion trap and passing the ions through the ion mobility spectrometer or separator in order to separate temporally the ions and applying a third time window and a fourth time window to ions emerging from the ion mobility spectrometer or separator, wherein the third time window is different to the first time window;

(vi) passing ions having drift times through the ion mobility spectrometer or separator falling within the third time window through ion mobility spectrometer or separator again in order to separate temporally the ions and again applying the third time window and the fourth time window to ions emerging from the ion mobility spectrometer or separator; and (vii) repeating step (vi) one or more times.

The method preferably further comprises the step of storing any ions having drift times through the ion mobility spectrometer or separator falling within the fourth time window in an ion trap.

According to an embodiment the first time window encompasses ions having drift times in the range $T1_{min}$-$T1_{max}$. The second time window encompasses ions having drift times $>T1_{max}$. The third time window encompasses ions having drift times in the range $T2_{min}$-$T2_{max}$ and wherein $T2_{max}>T1_{max}$. The fourth time window encompasses ions having drift times $>T2_{max}$.

According to an aspect of the present invention there is provided a mass spectrometer comprising:

an ion mobility spectrometer or separator;

an ion gate arranged downstream of the ion mobility spectrometer or separator; and a control system arranged and adapted:

(i) to cause ions to pass through the ion mobility spectrometer or separator in order to separate temporally the ions and to apply a first time window and a second time window to ions emerging from the ion mobility spectrometer or separator;

(ii) to cause ions having drift times through the ion mobility spectrometer or separator falling within the first time window to pass through the ion mobility spectrometer or separator again in order to separate temporally the ions and again to apply the first time window and the second time window to ions emerging from the ion mobility spectrometer or separator;

(iii) to cause any ions having drift times through the ion mobility spectrometer or separator falling within the second time window to be stored in an ion trap;

(iv) to repeat steps (ii) and (iii) one or more times; and then (v) to eject ions stored in the ion trap and to cause the ions to pass through the ion mobility spectrometer or separator in order to separate temporally the ions and to apply a third time window and a fourth time window to ions emerging from the ion mobility spectrometer or separator;

(vi) to cause ions having drift times through the ion mobility spectrometer or separator falling within the third time window to pass through ion mobility spectrometer or separator again in order to separate temporally the ions and again to apply the third time window and the fourth time window to ions emerging from the ion mobility spectrometer or separator; and (vii) to repeat step (vi) one or more times.

According to an aspect of the present invention there is provided a computer program executable by the control system of a mass spectrometer comprising an ion mobility spectrometer or separator and an ion gate arranged downstream of the ion mobility spectrometer or separator, the computer program being arranged to cause the control system:

(i) to cause a first group of ions to pass through the ion mobility spectrometer or separator in order to separate temporally at least some ions;

(ii) to operate the ion gate so that ions having drift times within a time window T1 are transmitted by the ion gate but ions having drift times outside of the time window T1 are not transmitted by the ion gate; and (iii) to cause at least some of the ions having drift times within the time window T1 to pass through the ion mobility spectrometer or separator again in order to separate temporally at least some of the ions.

According to an aspect of the present invention there is provided a computer readable medium comprising computer executable instructions stored on the computer readable medium, the instructions being arranged to be executable by a control system of a mass spectrometer comprising an ion mobility spectrometer or separator and an ion gate arranged downstream of the ion mobility spectrometer or separator, the computer program being arranged to cause the control system:

(i) to cause a first group of ions to pass through the ion mobility spectrometer or separator in order to separate temporally at least some ions;

(ii) to operate the ion gate so that ions having drift times within a time window T1 are transmitted by the ion gate but ions having drift times outside of the time window T1 are not transmitted by the ion gate; and (iii) to cause at least some of the ions having drift times within the time window T1 to pass through the ion mobility spectrometer or separator again in order to separate temporally at least some of the ions.

Preferably, the computer readable medium is selected from the group consisting of: (i) a ROM; (ii) an EAROM; (iii) an EPROM; (iv) an EEPROM; (v) a flash memory; (vi) an optical disk; (vii) a RAM; and (viii) a hard disk drive.

According to an aspect of the present invention there is provided a method of mass spectrometry comprising:

repeatedly passing ions through an ion mobility spectrometer or separator in order to separate temporally at least some of the ions and sampling ions emerging from the ion mobility spectrometer or separator with a first time window and a second time window, wherein ions having drift times within the first time window are passed again through the ion mobility spectrometer or separator in order to separate temporally at least some of the ions whereas ions having drift times within the second time window are temporarily stored in an ion trap;

mass analysing ions which emerge after having been passed repeatedly through the ion mobility spectrometer or separator;

releasing at least some of the ions which were temporarily stored in the ion trap;

repeatedly passing the ions through the ion mobility spectrometer or separator in order to separate temporally at least some of the ions and sampling ions emerging from the ion mobility spectrometer or separator with the first time window and the second time window, wherein ions having drift times within the second time window are passed again through the ion mobility spectrometer or separator in order to separate temporally at least some of the ions; and mass analysing ions which emerge after having been passed repeatedly through the ion mobility spectrometer or separator.

According to an aspect of the present invention there is provided a method of mass spectrometry comprising:

repeatedly passing ions through an ion mobility spectrometer or separator in order to separate temporally at least some of the ions and sampling ions emerging from the ion mobility spectrometer or separator with a first time window, wherein ions having drift times within the first time window are passed again through the ion mobility spectrometer or separator in order to separate temporally at least some of the ions whereas ions having drift times outside the first time window are temporarily stored in an ion trap;

mass analysing ions which emerge after having been passed repeatedly through the ion mobility spectrometer or separator;

releasing at least some of the ions which were temporarily stored in the ion trap;

repeatedly passing the ions through the ion mobility spectrometer or separator in order to separate temporally at least some of the ions and sampling ions emerging from the ion mobility spectrometer or separator with a second longer time window, wherein ions having drift times within the second time window are passed again through the ion mobility spectrometer or separator in order to separate temporally at least some of the ions; and mass analysing ions which emerge after having been passed repeatedly through the ion mobility spectrometer or separator.

According to another aspect of the present invention there is provided a method of mass spectrometry comprising:

passing ions through an ion mobility spectrometer or separator in order to separate temporally at least some of the ions;

applying a time window T1 to ions emerging from the ion mobility spectrometer or separator so that ions having drift times within the time window T1 form a first group of ions and are separated from ions having drift times outside of the time window T1 which form a second separate group of ions; and passing at least some of the first group of ions through the ion mobility spectrometer or separator again in order to separate temporally at least some of the first group of ions.

According to another aspect of the present invention there is provided a method of mass spectrometry comprising:

temporally separating a group of ions;

separating a first group of the ions which have drift times within a time window T1 from a second group of the ions which have drift times outside of the time window T1; and temporally separating again at least some of the first group of ions.

According to another aspect of the present invention there is provided a method of mass spectrometry comprising:

temporally separating an initial group of ions according to ion mobility;

segregating a first group of the separated initial group of ions which have drift times within a time window T1 from a remainder of the ions, the first group of ions including at least two types of ions having overlapping temporal distributions, wherein a concentration ratio of the at least two types of ions is greater in the segregated first group than in the initial group of ions;

temporally separating the segregated first group of the ions;

segregating a second group of the separated first group of ions which have drift times within the time window T1, or a different time window, wherein a concentration ratio of the at least two types of ions is greater in the second group than in the first group.

The method preferably further comprises temporally separating the segregated second group of ions to determine an ion mobility value of at least one of the ions.

According to a preferred embodiment of the present invention a travelling wave ion mobility spectrometer or separator is provided which is used to separate ions temporally. According to an embodiment the ion mobility spectrometer or separator may comprise a drift cell. Storage regions for storing ions are preferably provided at each end of the drift cell. For example, ions may be stored in one or more ion traps arranged upstream of the ion mobility spectrometer or separator. Ions may also be stored in one or more ion traps arranged downstream of the ion mobility spectrometer or separator.

According to an embodiment the ion mobility spectrometer may comprise a plurality of ring electrodes wherein transient DC voltages are applied to the ring electrodes in order to urge ions along the length of the ion mobility spectrometer or separator. Ions preferably pass through apertures in the ring electrodes. The ion mobility separator is preferably maintained at a relatively high pressure and ions are preferably separated according to their ion mobility in at least some modes of operation. Other modes of operation are contemplated wherein the ion mobility spectrometer may be operated in an ion guiding only mode of operation in order to transmit ions in a certain direction (e.g. upstream) without substantially separating ions according to their ion mobility.

The ion mobility spectrometer preferably comprises a plurality of electrodes, each electrode having an aperture through which ions are transmitted in use. Alternatively, the ion mobility spectrometer may comprise a segmented rod set.

The mass spectrometer preferably further comprises a device for applying or, maintaining a DC voltage gradient across at least a portion of the ion mobility spectrometer or separator.

The mass spectrometer preferably further comprises a device for applying an AC or RF voltage to at least some of the electrodes forming the ion mobility spectrometer or separator.

According to an embodiment the ion mobility spectrometer or separator may be maintained in use at a pressure selected from the group consisting of: (i) greater than or equal to 0.0001 mbar; (ii) greater than or equal to 0.0005 mbar; (iii) greater than or equal to 0.001 mbar; (iv) greater than or equal to 0.005 mbar; (v) greater than or equal to 0.01 mbar; (vi) greater than or equal to 0.05 mbar; (vii) greater than or equal to 0.1 mbar; (viii) greater than or equal to 0.5 mbar; (ix) greater than or equal to 1 mbar; (x) greater than or equal to 5 mbar; and (xi) greater than or equal to 10 mbar.

The ion mobility spectrometer or separator may be maintained in use at a pressure selected from the group consisting of: (i) less than or equal to 10 mbar; (ii) less than or equal to 5 mbar; (iii) less than or equal to 1 mbar; (iv) less than or equal to 0.5 mbar; (v) less than or equal to 0.1 mbar; (vi) less than or equal to 0.05 mbar; (vii) less than or equal to 0.01 mbar; (viii) less than or equal to 0.005 mbar; (ix) less than or equal to 0.001 mbar; (x) less than or equal to 0.0005 mbar; and (xi) less than or equal to 0.0001 mbar.

The ion mobility spectrometer or separator may be maintained, in use, at a pressure selected from the group consisting of: (i) between 0.0001 and 10 mbar; (ii) between 0.0001 and 1 mbar; (iii) between 0.0001 and 0.1 mbar; (iv) between 0.0001 and 0.01 mbar; (v) between 0.0001 and 0.001 mbar; (vi) between 0.001 and 10 mbar; (vii) between 0.001 and 1 mbar; (viii) between 0.001 and 0.1 mbar; (ix) between 0.001 and 0.01 mbar; (x) between 0.01 and 10 mbar; (xi) between 0.01 and 1 mbar; (xii) between 0.01 and 0.1 mbar; (xiii) between 0.1 and 10 mbar; (xiv) between 0.1 and 1 mbar; and (xv) between 1 and 10 mbar.

The ion mobility spectrometer or separator may be maintained, in use, at a pressure such that a viscous drag is imposed upon ions passing through the ion mobility spectrometer or separator.

One or more transient DC voltages or one or more transient DC voltage waveforms may be provided initially at a first axial position and are then provided subsequently at second, then third different axial positions along the length of ion mobility spectrometer or separator.

The one or more transient DC voltages or the one or more transient DC voltage waveforms may move from one end of the ion mobility spectrometer or separator to another end of the ion mobility spectrometer or separator so that at least some ions are urged along the ion mobility spectrometer or separator.

The one or more transient DC voltages or the one more transient DC voltage waveforms may be progressively applied along the ion mobility spectrometer or separator at a velocity of 10-250 m/s, 250-500 m/s, 500-750 m/s, 750-1000 m/s, 1000-1250 m/s, 1250-1500 m/s, 1500-1750 m/s, 1750-2000 m/s, 2000-2250, 2250-2500 m/s, 2500-2750 m/s, 2750-3000 m/s or >3000 m/s.

Two or more transient DC voltages or two or more transient DC voltage waveforms may pass simultaneously, along the ion mobility spectrometer or separator.

According to an embodiment a continuous beam of ions may be received at an entrance to the ion mobility spectrometer or separator. Alternatively, packets of ions may be received at an entrance to the ion mobility spectrometer or separator.

The ion mobility spectrometer or separator may comprise 10-20, 20-30, 30-40, 40-50, 50-60, 60-70, 70-80, 80-90, 90-100, 100-110, 110-120, 120-130, 130-140, 140-150 or more than 150 electrodes. At least 10%, 20%, 30%, 40%, 50%, 60%, 70%, 80%, 90%, or 95% of the electrodes forming the ion mobility spectrometer or separator are preferably connected to both a DC and an AC or RF voltage supply. Axially adjacent electrodes of the ion mobility spectrometer or separator are preferably supplied with AC or RF voltages having a phase difference of 180°. Other less preferred embodiments are contemplated wherein the phase difference may be <180°.

According to an embodiment the ion mobility spectrometer or separator may comprise a drift tube comprising one or more electrodes for maintaining an axial DC voltage gradient along at least a portion of the drift tube.

According to an embodiment the ion mobility spectrometer or separator may be arranged to cause ions to separate temporally according to their ion mobility.

The ion mobility spectrometer or separator may less preferably comprise a Field Asymmetric Ion Mobility Spectrometer ("FAIMS") which is arranged and adapted to cause ions to separate temporally according to their rate of change of ion mobility with electric field strength.

A buffer gas is preferably provided within the ion mobility spectrometer or separator.

The ion mobility spectrometer or separator preferably comprises a gas phase electrophoresis device.

The ion mobility spectrometer or separator may comprise a drift tube and one or more electrodes for maintaining an axial DC voltage gradient along at least a portion of the drift tube.

The ion mobility spectrometer or separator may comprise one or more multipole rod sets. For example, the ion mobility spectrometer or separator may comprise one or more quadrupole, hexapole, octapole or higher order rod sets.

The ion mobility spectrometer or separator may comprise one or more quadrupole, hexapole, octapole or higher order rod sets, wherein the one or more multipole rod sets are axially segmented, or comprise a plurality of axial segments.

At least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion mobility spectrometer or separator preferably have apertures through which ions are transmitted in use.

At least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion mobility spectrometer or separator preferably have apertures which are of substantially the same size or area.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion mobility spectrometer or separator have apertures which become progressively larger and/or smaller in size or in area in a direction along the axis of the ion mobility spectrometer or separator.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion mobility spectrometer or separator have apertures having internal diameters or dimensions selected from the group consisting of: (i) ≦1.0 mm; (ii) ≦2.0 mm; (iii) ≦3.0 mm; (iv) ≦4.0 mm; (v) ≦5.0 mm; (vi) ≦6.0 mm; (vii) ≦7.0 mm; (viii) ≦8.0 mm; (ix) ≦9.0 mm; (x) ≦10.0 mm; and (xi) >10.0 mm.

The ion mobility spectrometer or separator may comprise a plurality of plate or mesh electrodes and wherein at least some of the plate or mesh electrodes are arranged generally in the plane in which ions travel in use. The ion mobility spectrometer or separator may comprise a plurality of plate or mesh electrodes and wherein at least 5%, 10%, 15%, 20%, 25%, 30%, 35%, 40%, 45%, 50%, 55%, 60%, 65%, 70%, 75%, 80%, 85%, 90%, 95% or 100% of the plate or mesh electrodes are arranged generally in the plane in which ions travel in use. The ion mobility spectrometer or separator may comprise at least 2, 3, 4, 5, 6, 7, 8, 9, 10, 11, 12, 13, 14, 15, 16, 17, 18, 19, 20 or >20 plate or mesh electrodes.

The ion mobility spectrometer or separator may comprise at least 2, 3, 4, 5, 6, 7, 8, 9, 10, 11, 12, 13, 14, 15, 16, 17, 18, 19, 20 or >20 plate or mesh electrodes, wherein the plate or mesh electrodes are supplied with an AC or RF voltage wherein adjacent plate or mesh electrodes are supplied with opposite phases of the AC or RF voltage.

The ion mobility spectrometer or separator may comprise a plurality of axial segments or at least 5, 10, 15, 20, 25, 30, 35, 40, 45, 50, 55, 60, 65, 70, 75, 80, 85, 90, 95 or 100 axial segments.

The ion mobility spectrometer or separator may further comprise DC voltage means for maintaining a substantially constant DC voltage gradient along at least a portion of the axial length of the ion mobility spectrometer or separator.

According to an embodiment at least 1%, 5%, 10%, 20%, 30%, 40%, 50%, 60%, 70%, 80%, 90%, 95% or 100% of the electrodes forming the ion mobility spectrometer or separator are spaced apart from one another by an axial distance selected from the group consisting of: (i) less than or equal to 5 mm; (ii) less than or equal to 4.5 mm; (iii) less than or equal to 4 mm; (iv) less than or equal to 3.5 mm; (v) less than or equal to 3 mm; (vi) less than or equal to 2.5 mm; (vii) less than or equal to 2 mm; (viii) less than or equal to 1.5 mm; (ix) less than or equal to 1 mm; (x) less than or equal to 0.8 mm; (xi) less than or equal to 0.6 mm; (xii) less than or equal to 0.4 mm; (xiii) less than or equal to 0.2 mm; (xiv) less than or equal to 0.1 mm; and (xv) less than or equal to 0.25 mm.

At least some of the electrodes forming the ion mobility spectrometer or separator preferably comprise apertures and wherein the ratio of the internal diameter or dimension of the apertures to the centre-to-centre axial spacing between adjacent electrodes is selected from the group consisting of: (i) <1.0; (ii) 1.0-1.2; (iii) 1.2-1.4; (iv) 1.4-1.6; (v) 1.6-1.8; (vi) 1.8-2.0; (vii) 2.0-2.2; (viii) 2.2-2.4; (ix) 2.4-2.6; (x) 2.6-2.8; (xi) 2.8-3.0; (xii) 3.0-3.2; (xiii) 3.2-3.4; (xiv) 3.4-3.6; (xv) 3.6-3.8; (xvi) 3.8-4.0; (xvii) 4.0-4.2; (xviii) 4.2-4.4; (xix) 4.4-4.6; (xx) 4.6-4.8; (xxi) 4.8-5.0; and (xxii) >5.0.

The ion mobility spectrometer or separator preferably has a length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; and (xi) >200 mm.

Preferably at least 1%, 5%, 10%, 20%, 30%, 40%, 50%, 60%, 70%, 80%, 90%, 95% or 100% of the electrodes forming the ion mobility spectrometer or separator have a thickness or axial length selected from the group consisting of: (i) less than or equal to 5 mm; (ii) less than or equal to 4.5 mm; (iii) less than or equal to 4 mm; (iv) less than or equal to 3.5 mm; (v) less than or equal to 3 mm; (vi) less than or equal to 2.5 mm; (vii) less than or equal to 2 mm; (viii) less than or equal to 1.5 mm; (ix) less than or equal to 1 mm; (x) less than or equal to 0.8 mm; (xi) less than or equal to 0.6 mm; (xii) less than or equal to 0.4 mm; (xiii) less than or equal to 0.2 mm; (xiv) less than or equal to 0.1 mm; and (xv) less than or equal to 0.25 mm.

According to an embodiment the ion mobility spectrometer may further comprise:

(i) a device for applying one or more DC voltages to the electrodes forming the ion mobility spectrometer or separator and/or to auxiliary electrodes so that in a mode of operation a substantially constant DC voltage gradient is maintained along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator; and/or (ii) a device for applying multi-phase RF voltages to the electrodes forming the ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

According to an embodiment the apparatus may comprise a first RF device arranged and adapted to apply a first AC or RF voltage having a first frequency and a first amplitude to at least some of the electrodes forming the ion mobility spectrometer or separator such that, in use, ions are confined radially within the ion mobility spectrometer or separator.

The first frequency is preferably selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The first amplitude is preferably selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

In a mode of operation adjacent or neighbouring electrodes forming the ion mobility spectrometer or separator electrodes are preferably supplied with opposite phase of the first AC or RF voltage.

According to an embodiment the ion mobility spectrometer may comprise 1-10, 10-20, 20-30, 30-40, 40-50, 50-60, 60-70, 70-80, 80-90, 90-100 or >100 groups of electrodes, wherein each group of electrodes comprises at least 1, 2, 3, 4, 5, 6, 7, 8, 9, 10, 11, 12, 13, 14, 15, 16, 17, 18, 19 or 20 electrodes and wherein at least 1, 2, 3, 4, 5, 6, 7, 8, 9, 10, 11, 12, 13, 14, 15, 16, 17, 18, 19 or 20 electrodes in each group are supplied with the same phase of the first AC or RF voltage.

The apparatus preferably further comprises a device arranged and adapted either:

(i) to generate a linear axial DC electric field along at least 1%, 5%, 10%, 20%, 30%, 40%, 50%, 60%, 70%, 80%, 90%, 95% or 100% of the axial length of the ion mobility spectrometer or separator; or (ii) to generate a non-linear or stepped axial DC electric field along at least 1%, 5%, 10%, 20%, 30%, 40%, 50%, 60%, 70%, 80%, 90%, 95% or 100% of the axial length of the ion mobility spectrometer or separator.

According to an embodiment the residence, transit or reaction time of at least 1%, 5%, 10%, 20%, 30%, 40%, 50%, 60%, 70%, 80%, 90%, 95% or 100% of ions passing through the ion mobility spectrometer or separator is preferably selected from the group consisting of: (i) <1 ms; (ii) 1-5 ms; (iii) 5-10 ms; (iv) 10-15 ms; (v) 15-20 ms; (vi) 20-25 ms; (vii) 25-30 ms; (viii) 30-35 ms; (ix) 35-40 ms; (x) 40-45 ms; (xi) 45-50 ms; (xii) 50-55 ms; (xiii) 55-60 ms; (xiv) 60-65 ms; (xv) 65-70 ms; (xvi) 70-75 ms; (xvii) 75-80 ms; (xviii) 80-85 ms; (xix) 85-90 ms; (xx) 90-95 ms; (xxi) 95-100 ms; (xxii) 100-105 ms; (xxiii) 105-110 ms; (xxiv) 110-115 ms; (xxv) 115-120 ms; (xxvi) 120-125 ms; (xxvii) 125-130 ms; (xxviii) 130-135 ms; (xxix) 135-140 ms; (xxx) 140-145 ms; (xxxi) 145-150 ms; (xxxii) 150-155 ms; (xxxiii) 155-160 ms; (xxxiv) 160-165 ms; (xxxv) 165-170 ms; (xxxvi) 170-175 ms; (xxxvii) 175-180 ms; (xxxviii) 180-185 ms; (xxxix) 185-190 ms; (xl) 190-195 ms; (xli) 195-200 ms; and (xlii) >200 ms.

The ion mobility spectrometer or separator preferably has a cycle time selected from the group consisting of: (i) <1 ms; (ii) 1-10 ms; (iii) 10-20 ms; (iv) 20-30 ms; (v) 30-40 ms; (vi) 40-50 ms; (vii) 50-60 ms; (viii) 60-70 ms; (ix) 70-80 ms; (x) 80-90 ms; (xi) 90-100 ms; (xii) 100-200 ms; (xiii) 200-300 ms; (xiv) 300-400 ms; (xv) 400-500 ms; (xvi) 500-600 ms; (xvii) 600-700 ms; (xviii) 700-800 ms; (xix) 800-900 ms; (xx) 900-1000 ms; (xxi) 1-2 s; (xxii) 2-3 s; (xxiii) 3-4 s; (xxiv) 4-5 s; and (xxv) >5 s.

According to an embodiment the first upstream ion trap and/or the second upstream ion trap and/or the downstream ion trap may comprise an ion tunnel ion trap comprising a plurality of electrodes having apertures through which ions are transmitted in use or a quadrupole rod set (or Paul) ion trap.

The ion gate preferably comprises a non-destructive ion gate although according to less preferred embodiments the ion gate may comprise a destructive ion gate in at least some modes of operation wherein ions impinge upon the ion gate and are lost to the system. According to the preferred embodiment the ion gate comprises an electrode having an aperture through which ions are transmitted. The ion gate is switched ON by applying a voltage >2 V or >10 V higher than the potential of the exit region of the ion mobility spectrometer or separator. As a result, ions are repelled by the ion gate and are prevented from passing through the ion gate to reach the downstream ion trap.

According to an embodiment the mass spectrometer may comprise one or more ion sources selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) a sub-atmospheric pressure Electrospray ionisation ion source; and (xxii) a Direct Analysis in Real Time ("DART") ion source.

The mass spectrometer may comprise one or more continuous or pulsed ion sources.

The mass spectrometer may comprise one or more ion guides.

According to an embodiment the mass spectrometer may further comprise one or more ion mobility separation devices and/or one or more Field Asymmetric Ion Mobility Spectrometer devices.

The mass spectrometer may comprise one or more ion traps or one or more ion trapping regions.

According to an embodiment the mass spectrometer may further comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device. The collision, fragmentation or reaction cell may be arranged upstream and/or downstream of the ion mobility spectrometer or separator.

According to an embodiment the mass spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

According to an embodiment the mass spectrometer may further comprise one or more energy analysers or electrostatic energy analysers.

According to an embodiment the mass spectrometer may further comprise one or more ion detectors.

According to an embodiment the mass spectrometer may further comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter.

According to an embodiment the mass spectrometer may further comprise a device or ion gate for pulsing ions.

According to an embodiment the mass spectrometer may further comprise a device for converting a substantially continuous ion beam into a pulsed ion beam.

According to an embodiment the mass spectrometer may further comprise a C-trap and an orbitrap (RTM) mass analyser comprising an outer barrel-like electrode and a coaxial inner spindle-like electrode. In a first mode of operation ions may be transmitted to the C-trap and are then injected into the orbitrap (RTM) mass analyser. In a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the orbitrap (RTM) mass analyser.

According to an embodiment the mass spectrometer may comprise a stacked ring ion guide comprising a plurality of electrodes each having an aperture through which ions are transmitted in use and wherein the spacing of the electrodes increases along the length of the ion path. The apertures in the electrodes in an upstream section of the ion guide preferably have a first diameter and the apertures in the electrodes in a downstream section of the ion guide preferably have a second diameter which is smaller than the first diameter. Opposite phases of an AC or RF voltage are preferably applied, in use, to successive electrodes.

Various embodiments of the present invention will now be described, by way of example only, and with reference to the accompanying drawings in which.

Figure 8:
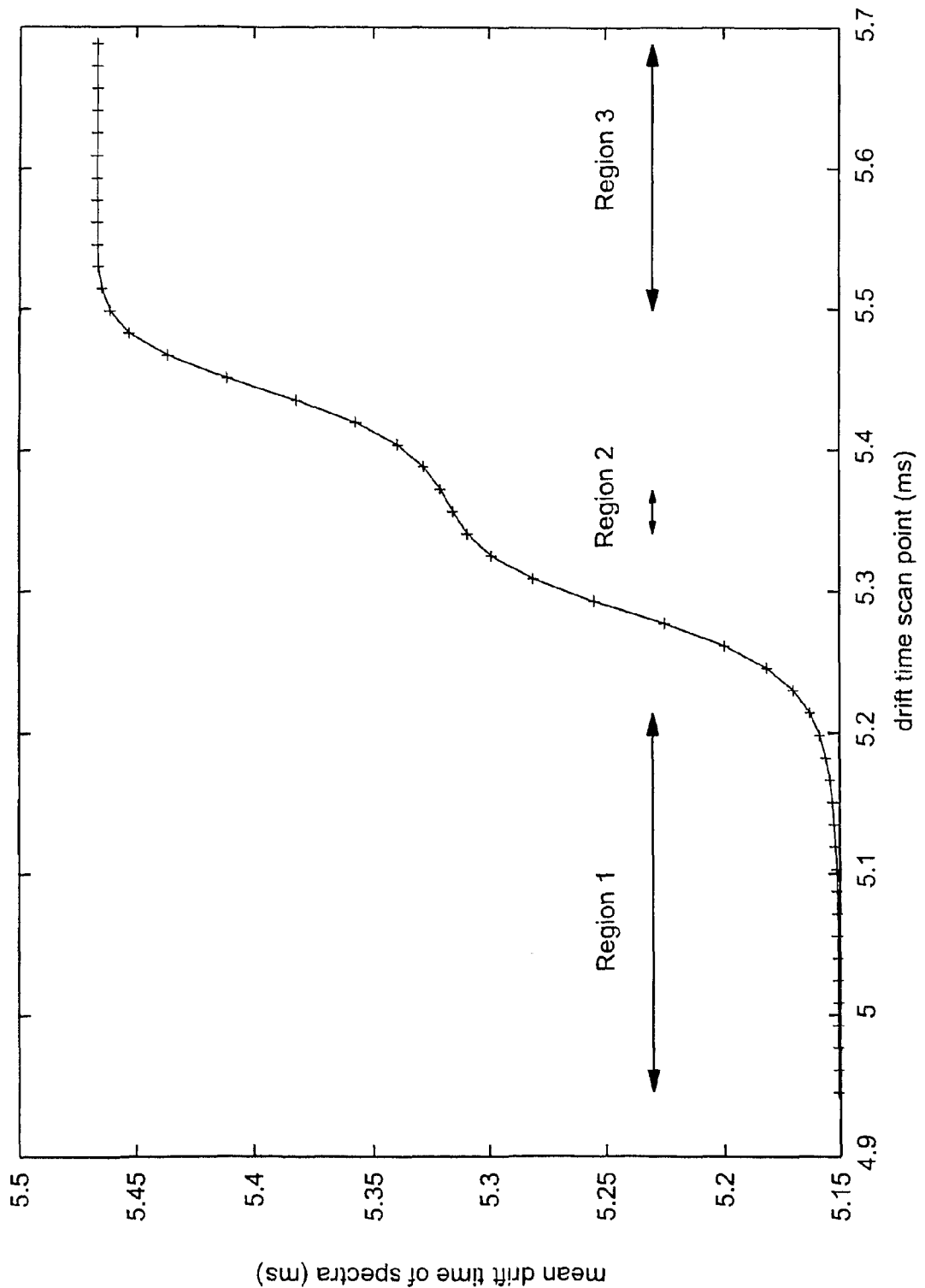
FIG. 8 shows a plot of mean drift time versus drift time scan point for the three ion populations as illustrated in FIG. 7 wherein regions corresponding to a single ion species are identified by limiting the gradient between successive points to be less than 0.4.
Figure 9A:
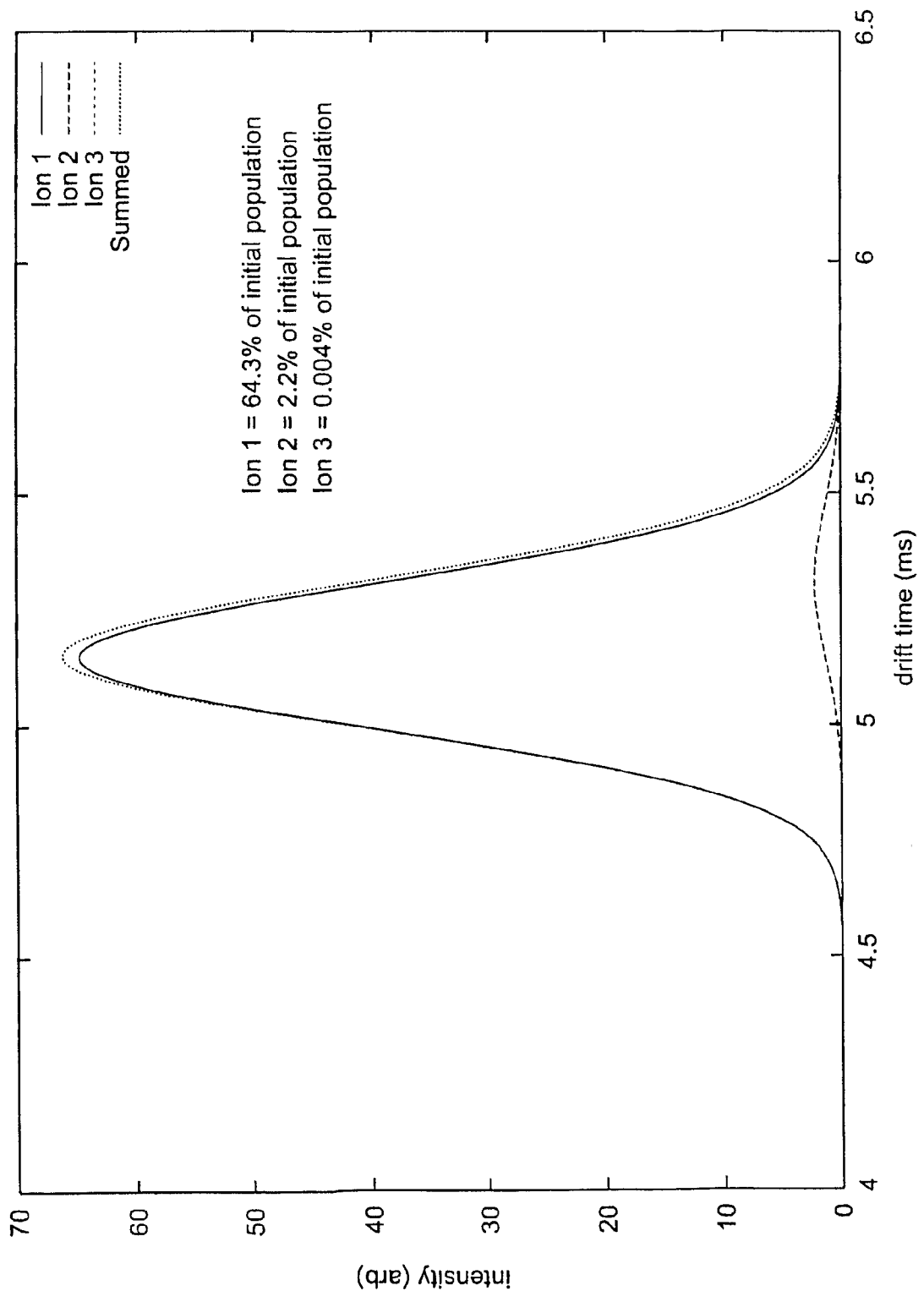
Figure 9B:
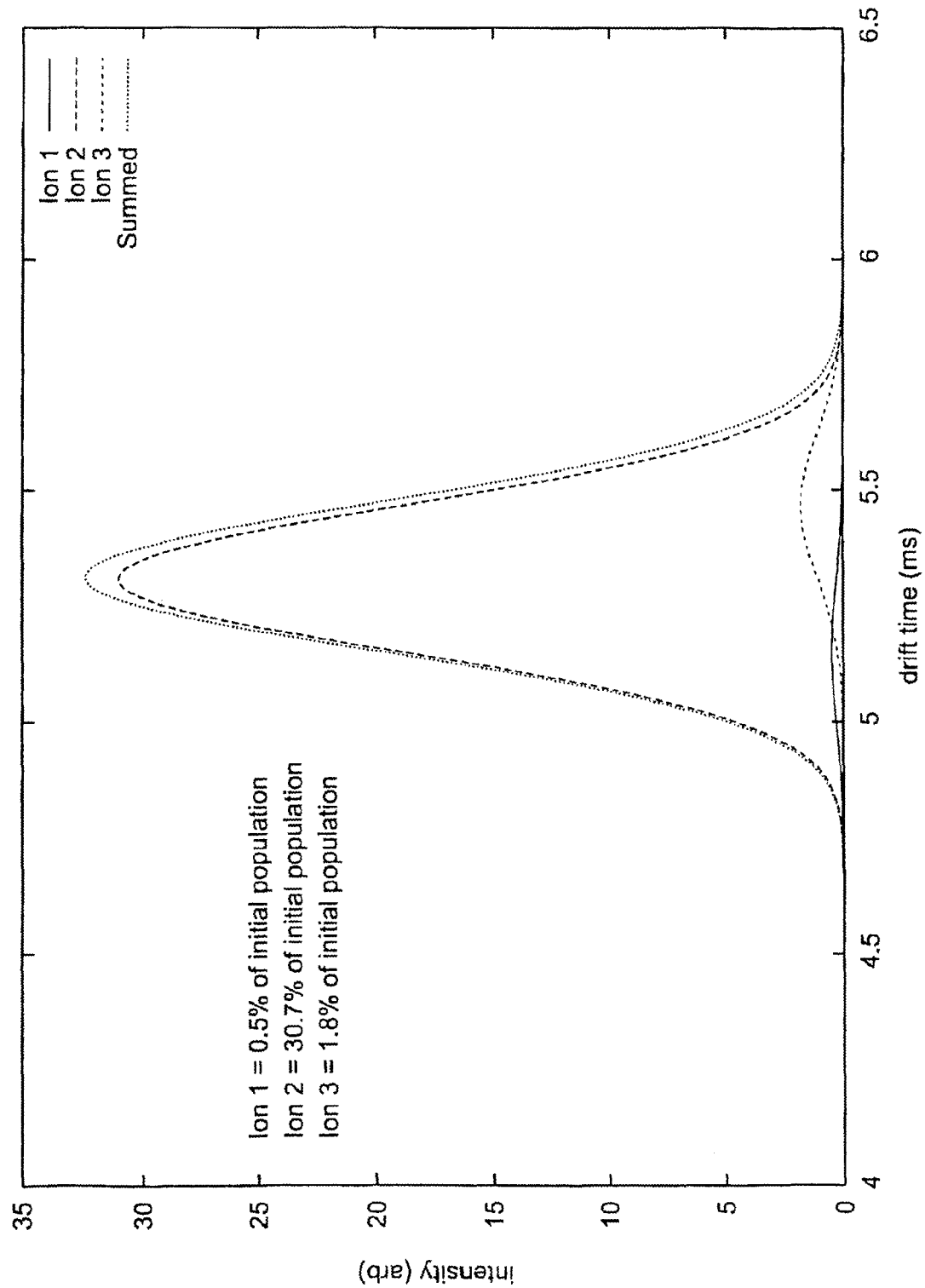
Figure 9C:
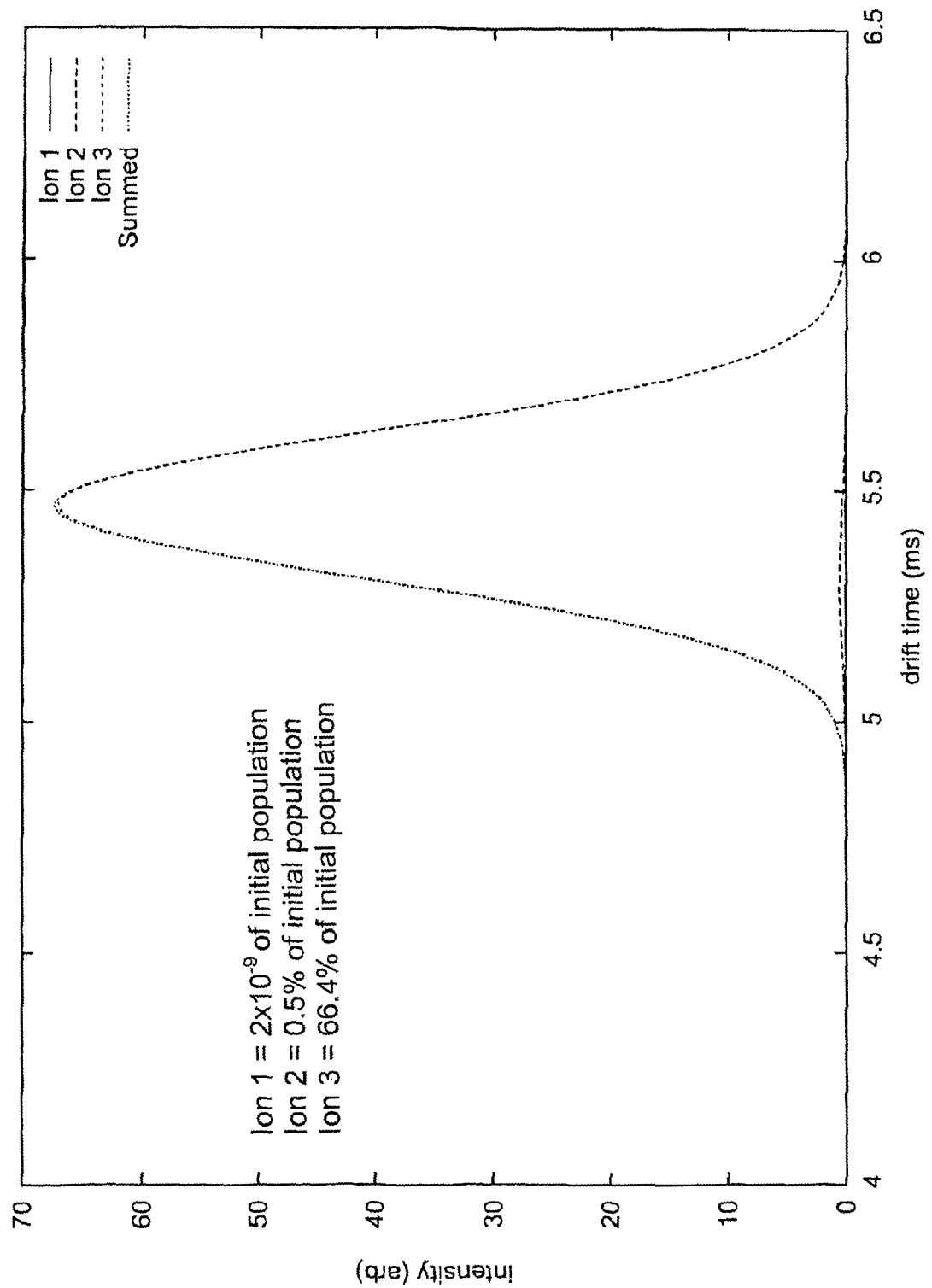
Figure 10:
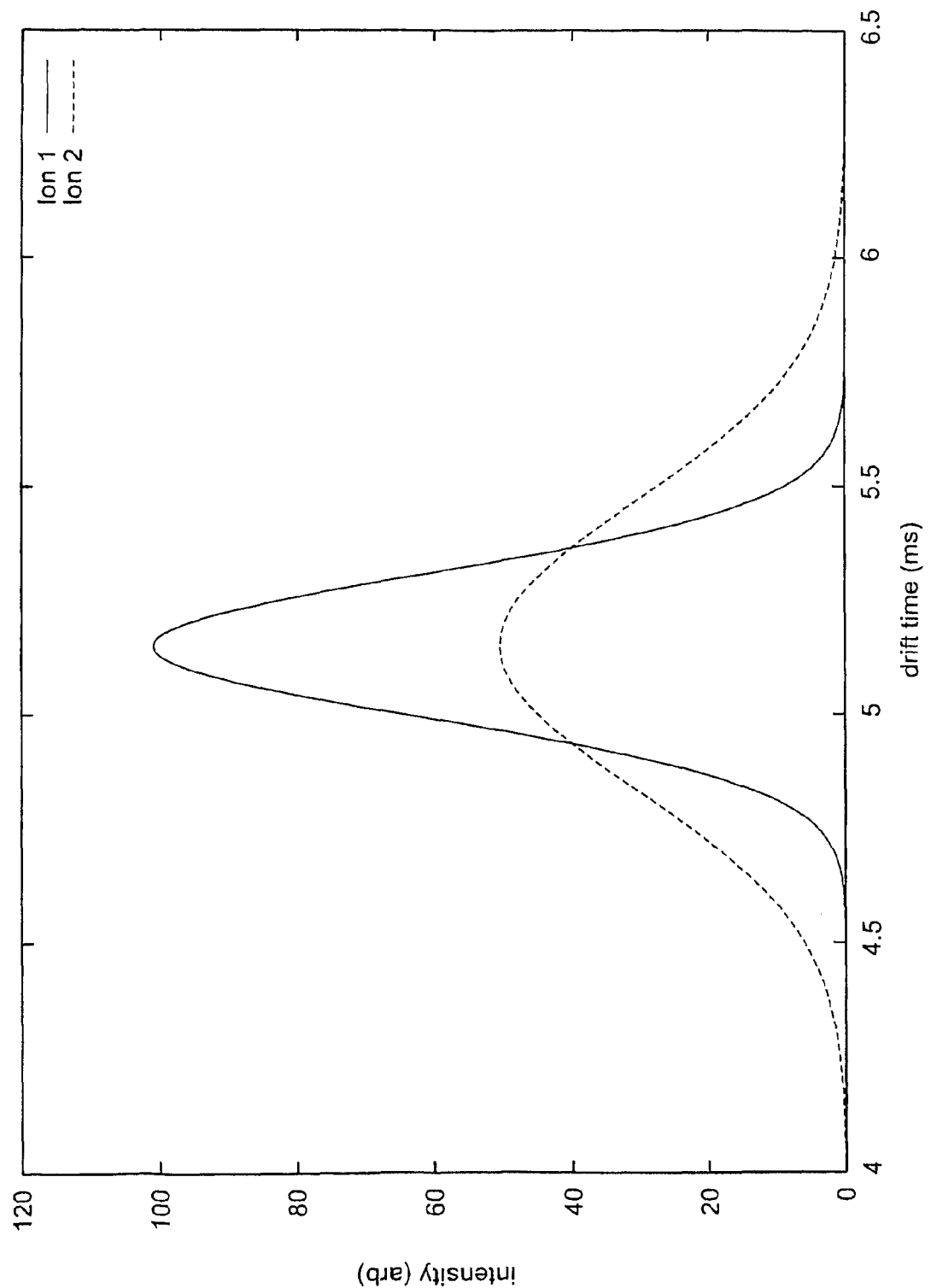
Figure 11:
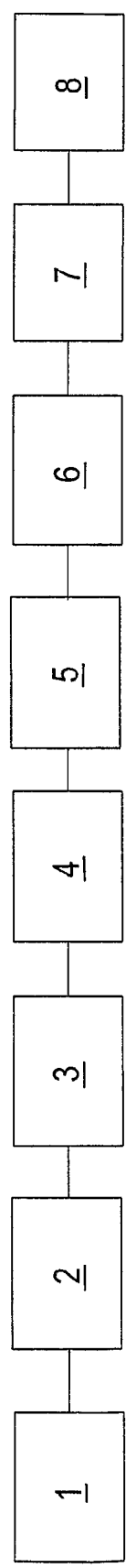
Figure 12:
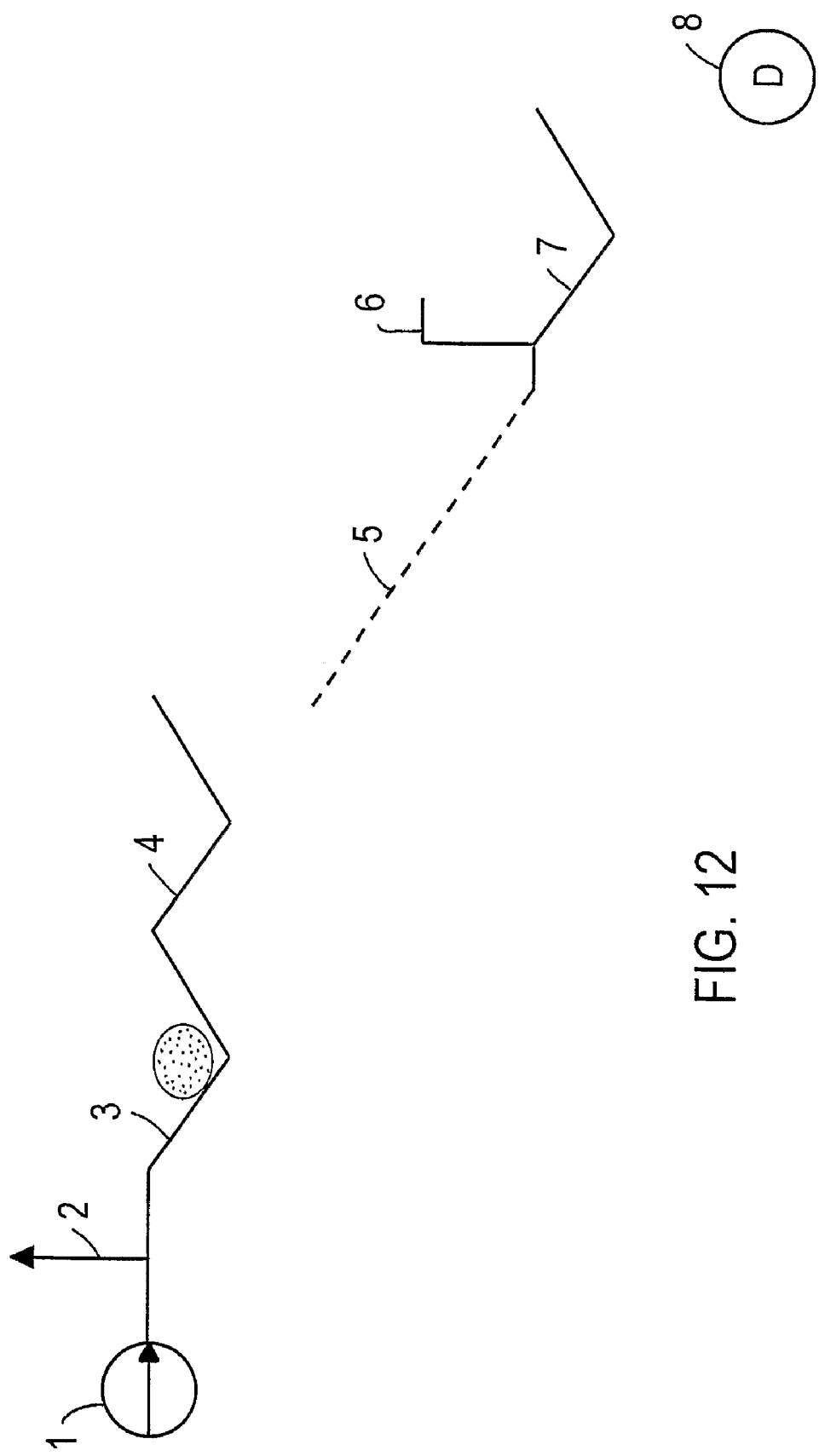
Figure 13:
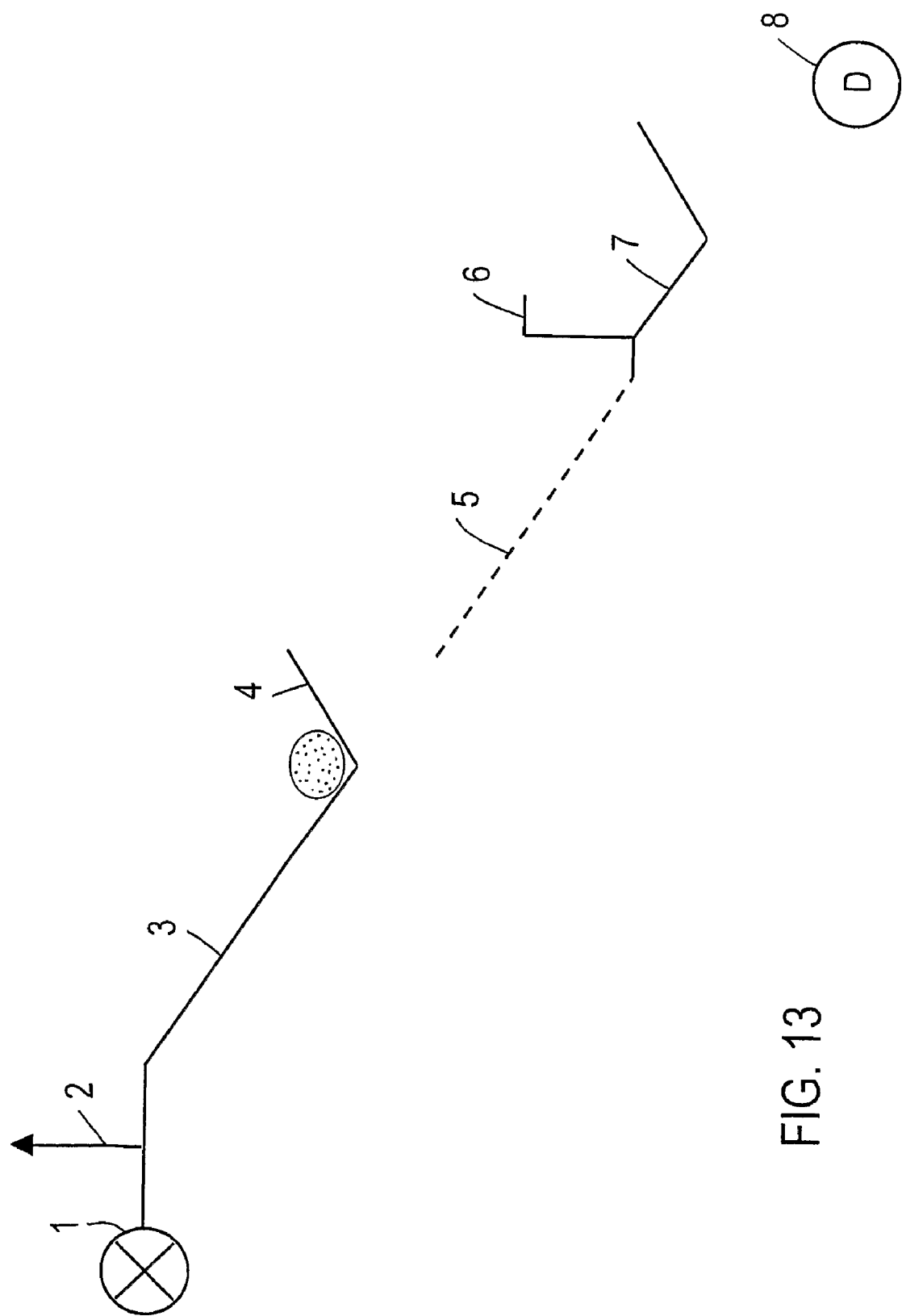
Figure 14:
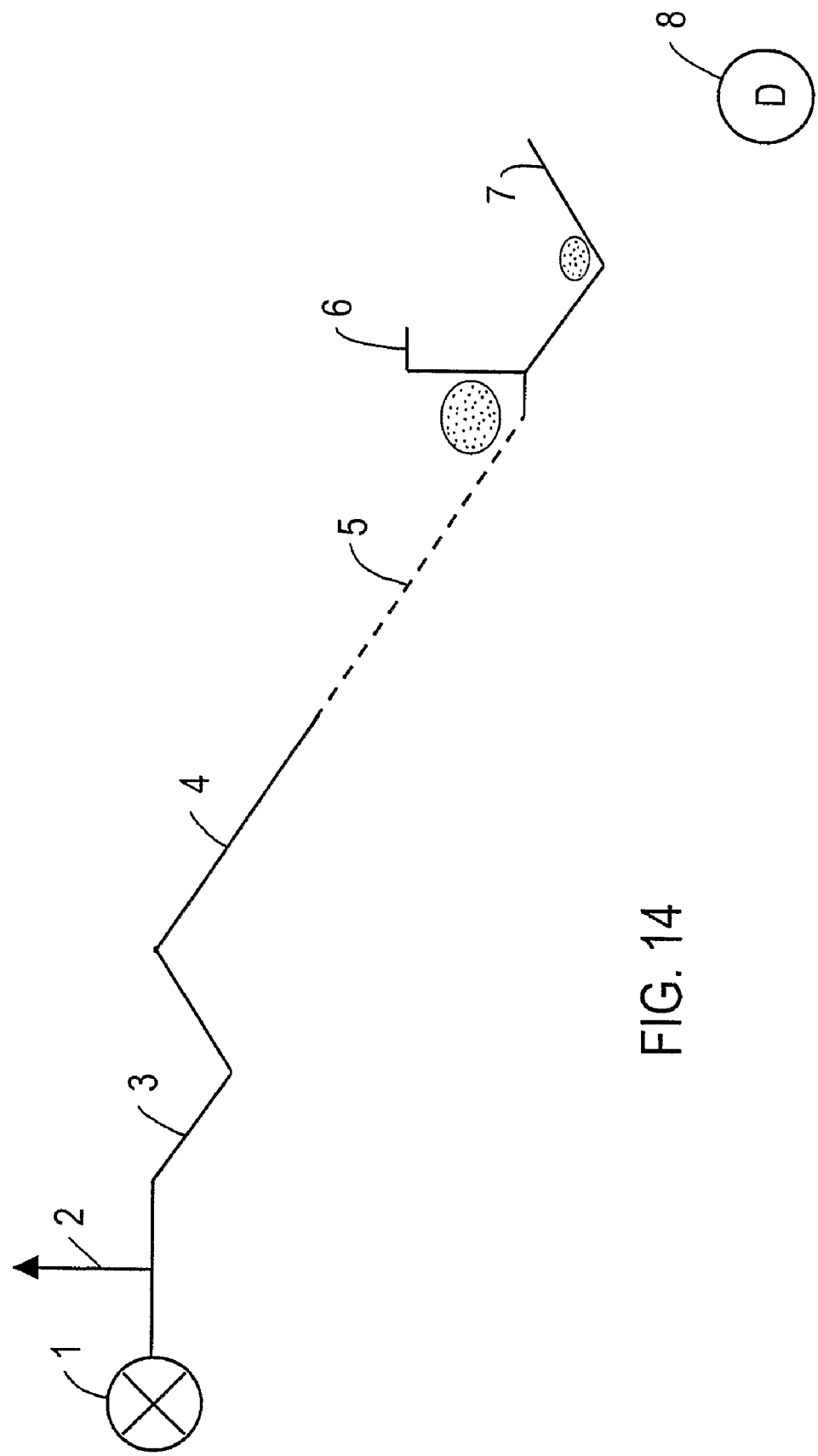
Figure 15:
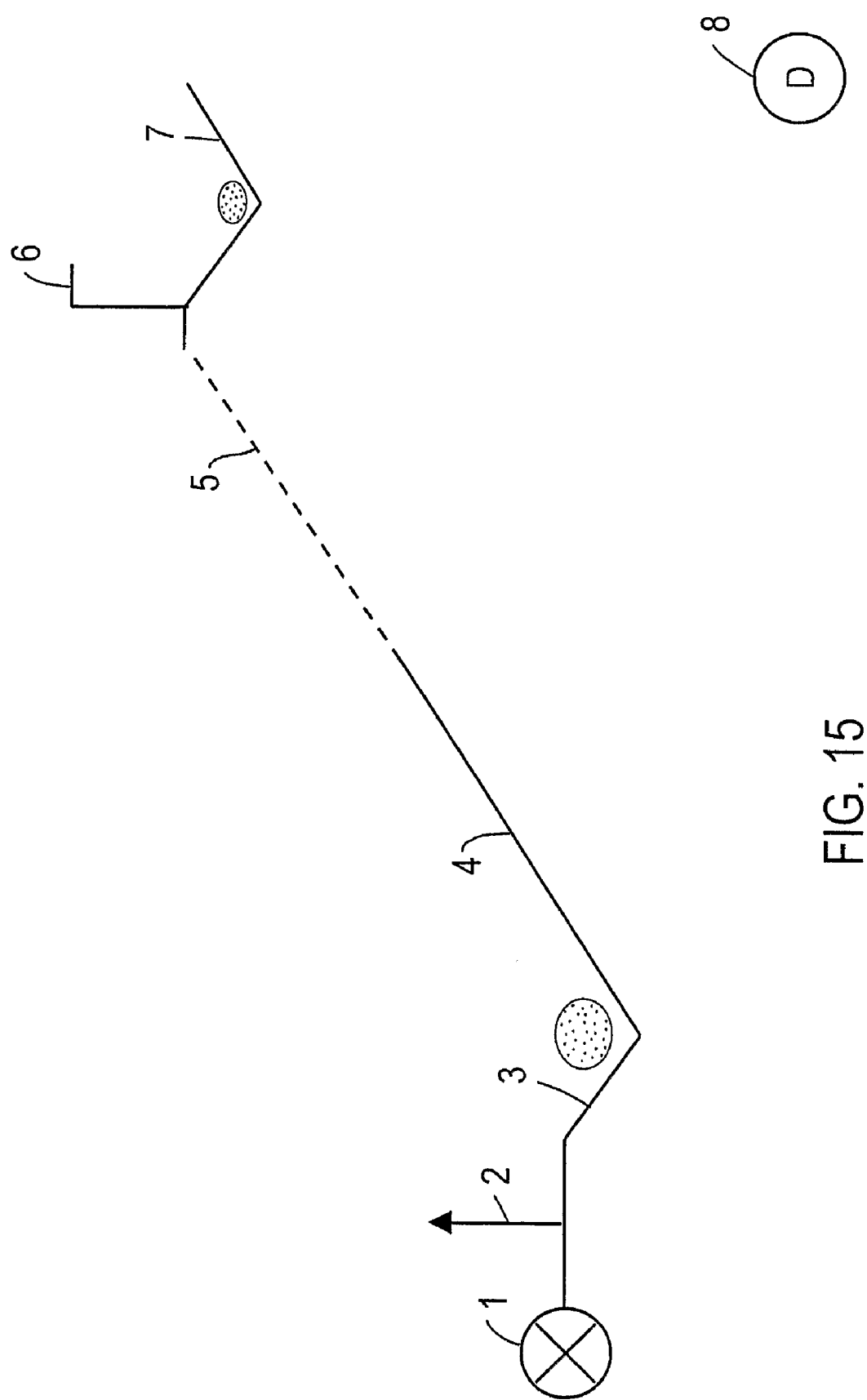
Figure 16:
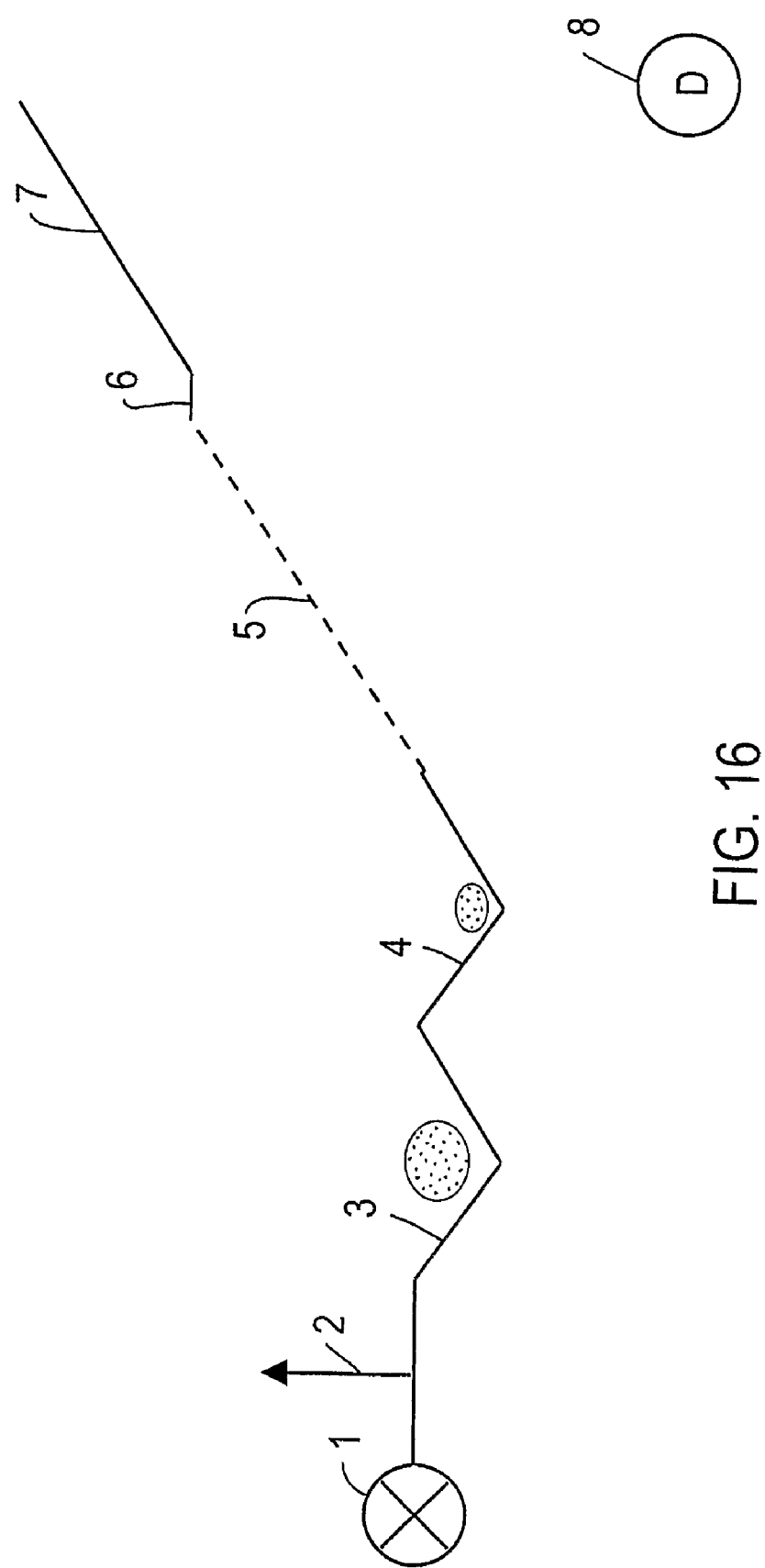
Figure 17:
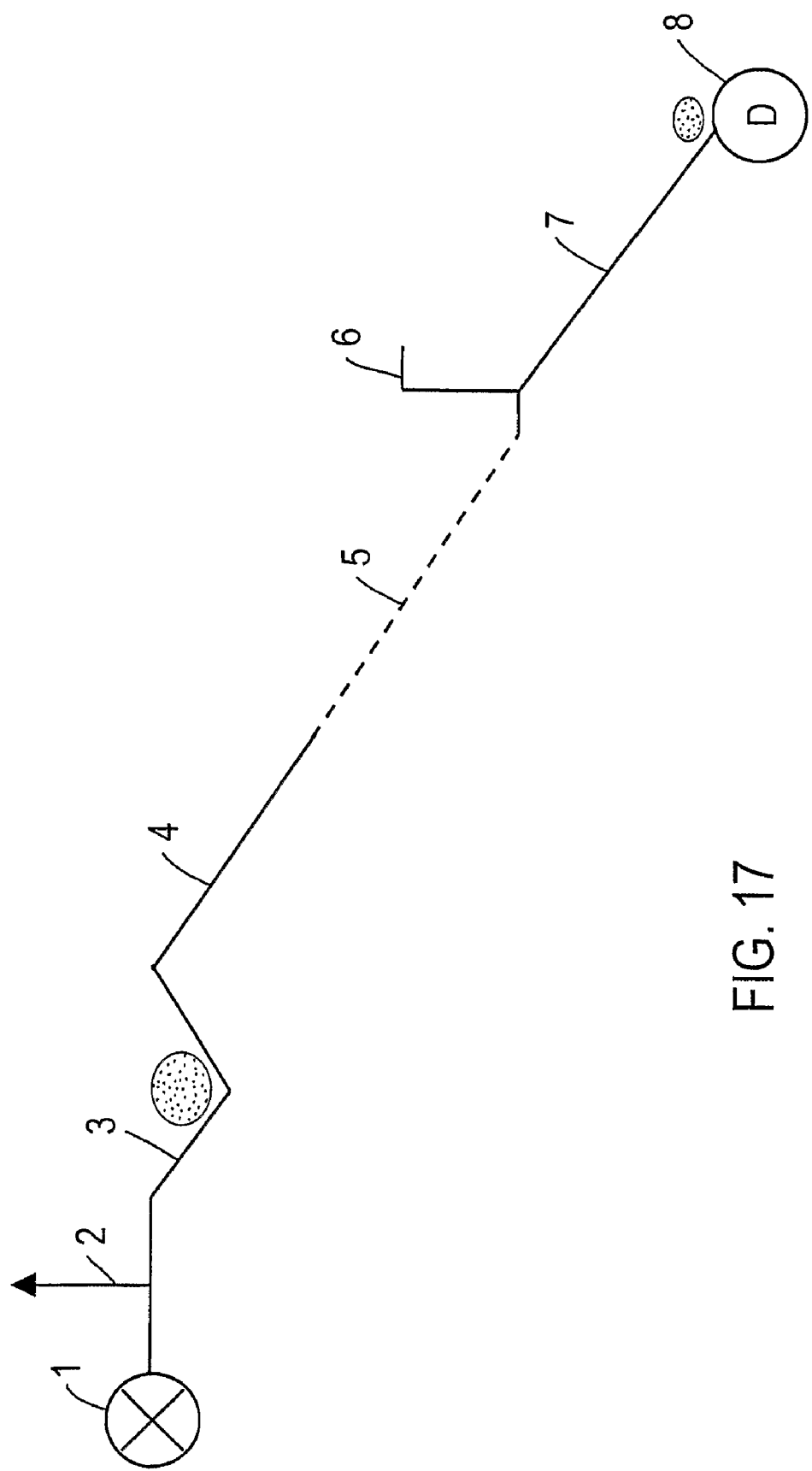
Figure 18:
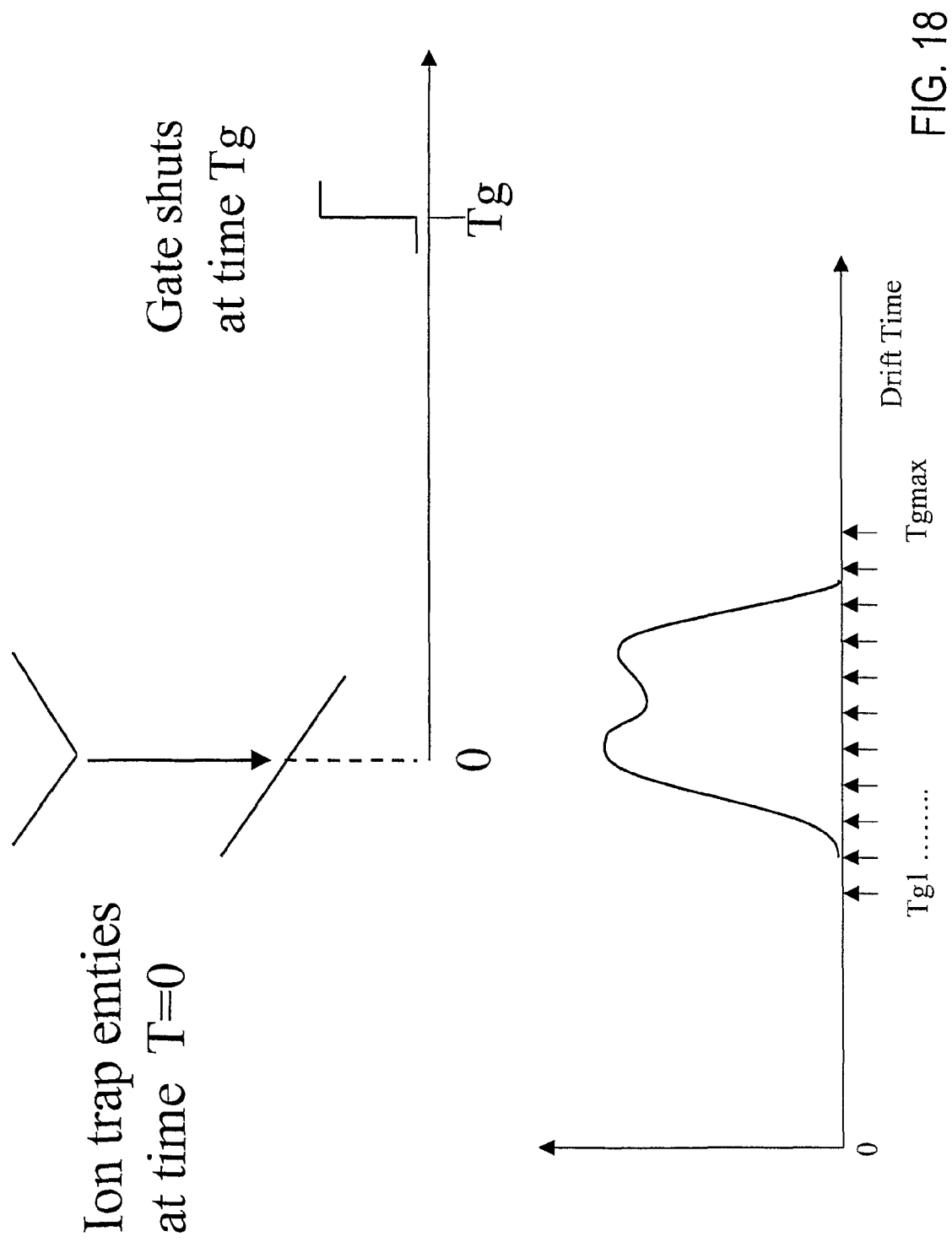
Figure 19:
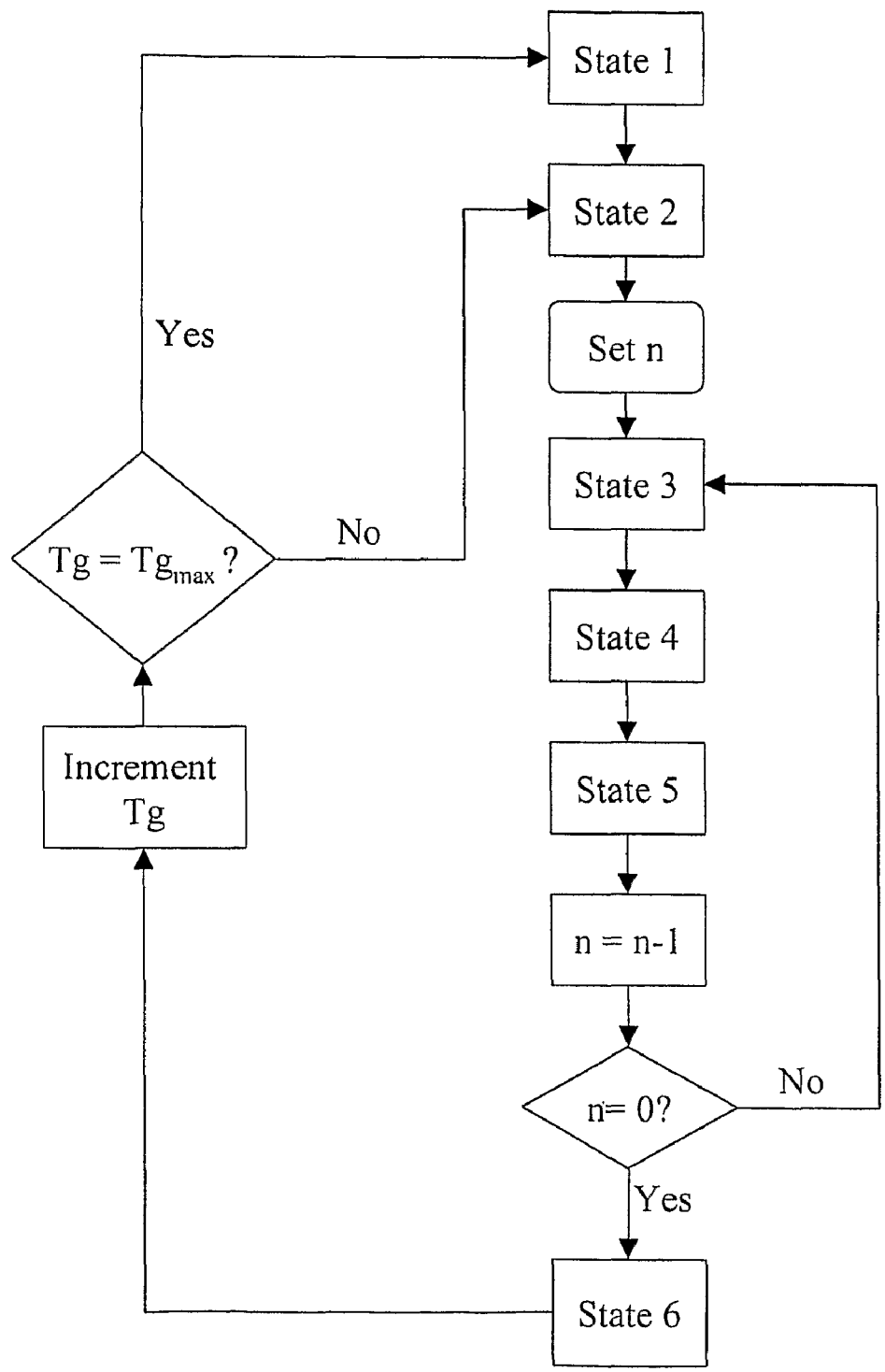

FIG. 9A shows individual and summed drift time spectra from the first region shown in FIG. 8 indicating that the ions substantially comprise the first ion species, FIG. 9B shows individual and summed drift time spectra from the second region shown in FIG. 8 indicating that the ions substantially comprise the second ion species and FIG. 9C shows individual and summed drift time spectra from the third region shown in FIG. 8 indicating that the ions substantially comprise the third ion species;

FIG. 10 shows drift times for two ion populations having identical mean drift times but differing standard deviations according to a third embodiment of the present invention;

FIG. 11 shows a mass spectrometer according to an embodiment of the present invention;

FIG. 12 illustrates an aspect of the preferred embodiment wherein ions are selected by a mass filter and are stored in a first upstream ion trap;

FIG. 13 illustrates an aspect of the preferred embodiment wherein ions are moved from a first upstream ion trap to a second upstream ion trap;

FIG. 14 illustrates an aspect of the preferred embodiment wherein mobility separated ions are gated and ions transmitted by the ion gate are stored in a downstream ion trap;

FIG. 15 illustrates an aspect of the preferred embodiment wherein un-gated ions are sent back upstream to a first upstream ion trap;

FIG. 16 illustrates an aspect of the preferred embodiment wherein gated ions are sent back upstream to a second upstream ion trap;

FIG. 17 illustrates an aspect of the preferred embodiment wherein the gated ion population is passed back through the ion mobility spectrometer and the ions are detected by a downstream ion detector after a conventional ion mobility scan;

FIG. 18 illustrates the timing relationship between ions being released from a second upstream ion trap at a time T=0 and the subsequent closure of an ion gate at a time $T=T_g$ and also shows how the delay time $T_g$ may be progressively increased according to the second embodiment; and FIG. 19 shows a flow chart illustrating different aspects of a preferred embodiment of the present invention.

A first embodiment of the present invention will now be described. Two different species of ions having different ion mobilities may be considered. The two ion species are preferably passed through a drift cell or an ion mobility spectrometer or separator. According to the preferred embodiment the drift cell or ion mobility spectrometer or separator comprises a plurality of ring electrodes having apertures through which ions are transmitted in use. One or more transient DC voltages or potentials are preferably applied to the electrodes of the drift cell or ion mobility spectrometer in order to urge ions along and through the length of the drift cell or ion mobility separator. As a result, ions will begin to separate temporally according to their ion mobility as they pass through the drift cell or ion mobility spectrometer or separator.

If a single species of ion is passed through the drift cell or ion mobility separator then the ions will preferably exit or emerge from the drift cell or ion mobility separator with a drift time distribution that is approximately Gaussian and with a mean and standard deviation that is related to the mobility of the ions, the gas pressure in the drift cell or ion mobility separator and the parameters of the transient DC voltages which are preferably applied to the electrodes of the drift cell or ion mobility spectrometer or separator.

According to the first embodiment a population of ions may be passed into a drift cell or ion mobility spectrometer or separator and a non-destructive ion gate may be arranged at the exit of the drift cell or ion mobility spectrometer or separator. As discussed in more detail below, the ions may be sampled initially by applying a first time window and may then be sampled by applying a second time window. When the ion gate is switched OFF then ions are onwardly transmitted by the ion gate and when the ion gate is switched ON then ions are preferably prevented from being onwardly transmitted by the ion gate so that the ions become trapped within the exit region of the ion mobility spectrometer or separator upstream of the ion gate.

According to an embodiment the ion gate is switched from OFF to ON after a delay time T=T1 as measured from the time when ions are first injected into the drift cell or ion mobility spectrometer (at a time T=0) from an upstream ion trap. According to the first embodiment a first time window is applied by allowing ions to be transmitted by the ion gate between time T=0 to time T=T1. As a result, only a section or proportion of the ions which are injected into the drift cell or ion mobility spectrometer will exit the drift cell or ion mobility spectrometer before the ion gate blocks the onward transmission of ions at time T=T1.

According to an embodiment of the present invention two ion populations or two different ion species may be considered as being simultaneously injected into the drift cell or ion mobility spectrometer or separator. The ions are then caused to separate temporally according to their ion mobility. The ions transmitted by the ion gate can be considered as comprising two ion populations R1,R2. The first ion population R1 corresponds to the first species of ion and hence the first ion population R1 will be given by the overlap of the Gaussian drift time distribution of the first ions and the first drift time window during which ions were transmitted by the ion gate. Similarly, the second ion population R2 corresponds to the second species of ion and hence the second ion population R2 will be given by the overlap of the Gaussian drift time distribution of the second ions and the first drift time window during which ions were transmitted by the ion gate. The ratio of the two ion populations transmitted by the ion gate is therefore given by R1/R2.

The two ions populations R1,R2 which are transmitted by the ion gate and which therefore exit the drift cell or ion mobility spectrometer are preferably recompressed i.e. any drift time separation can be collapsed. This group of ions is then preferably returned to the entrance of the drift cell or ion mobility spectrometer and the ions are then again passed back through the drift cell or ion mobility spectrometer or separator. The ion gate is then again switched from OFF to ON after the same delay time T1. As a result, ions are again selected with the same first drift time window so that the ratio of the two ion populations after a second effective pass through the drift cell or ion mobility separator will be given be $(R1/R2)^2$. It will be apparent that if this process is repeated then after n passes through the drift cell or ion mobility separator then the ion population ratio will be given by $(R1/R2)^n$. It is therefore apparent that by passing ions multiple times through the drift cell or ion mobility spectrometer and by closing the ion gate after the same delay time T1 each time then the proportion of one population of ions with respect to another population of ions can be attenuated.

After a desired number of passes through the drift cell or ion mobility spectrometer the ions may then be passed through the drift cell or ion mobility spectrometer a final time. When the ions are passed through the drift cell or ion mobility spectrometer for the final time then according to an embodiment of the present invention no drift time window is imposed i.e. the ion gate remains OFF. As a result, the ions are preferably subjected to a conventional ion mobility scan wherein the drift time peaks of all the ions which are separated temporally as they pass through the drift cell or ion mobility spectrometer are determined.

According to the preferred embodiment those ions which are not transmitted by the ion gate at any stage are not lost. Instead, those ions which are not transmitted by the ion gate during any of the n scans which are performed are preferably retained in an ion trap. According to an embodiment those ions which are not transmitted by the ion gate are preferably initially trapped at an exit region of the ion mobility spectrometer by the ion gate. The ions may then be transferred to an upstream ion trap and stored whilst those ions which are transmitted by the ion gate are processed. According to the first embodiment once the initial process of passing ions transmitted by the ion gate back through the ion mobility spectrometer or separator multiple times has been completed and a final ion mobility scan has been performed, then the ions stored in the upstream ion trap which correspond with ions which were previously blocked by the ion gate are then processed and repeatedly sampled using a second drift window so that only ions having drift times in a second drift window are retained. Those ions which have drift times within the first drift window are preferably not retained.

Figure 1:
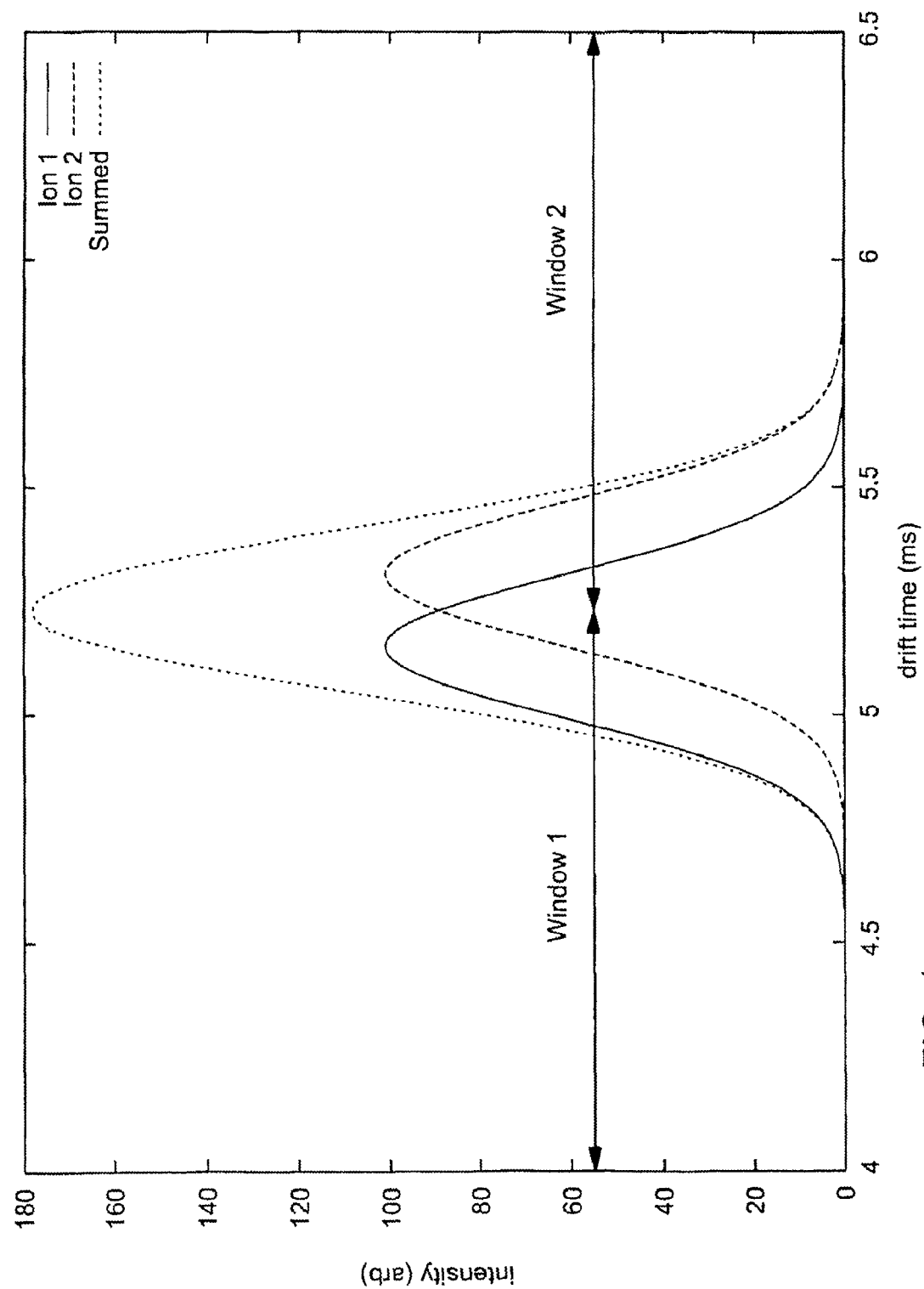
FIG. 1 shows individual and summed Gaussian drift time peaks for two ions having the same standard deviation according to an embodiment wherein the mean peaks are separated by one standard deviation.

In order to further illustrate aspects of the first embodiment two ion populations are shown in FIG. 1 having different average drift times through an ion mobility spectrometer or separator. FIG. 1 shows the drift time peaks of the two ion species after one pass through a drift cell or ion mobility spectrometer or separator. In the example shown in FIG. 1 the two ion species have the same standard deviation and the mean drift times of the two species of ions are separated by one standard deviation. FIG. 1 also shows a summed plot obtaining by combining the two ion distributions and demonstrates that the two species of ions will remain unresolved after a single pass through the drift cell or ion mobility spectrometer or separator.

According to the first embodiment two drift time or sampling windows are imposed upon the ions as they pass through the drift cell or ion mobility spectrometer or separator. The first drift time window (Window 1 as shown in FIG. 1) preferably encompasses ions having drift times up to the time corresponding with the mid point between the two ion peaks i.e. the mean drift time of the summed peak (5.25 ms). The first drift time or sampling window therefore encompasses ions having a drift time through the drift cell or ion mobility spectrometer in the range 0-5.25 ms.

The second drift time or sampling window (Window 2 as shown in FIG. 1) preferably encompasses ions having drift times longer than the mean drift time of the summed peak and hence encompasses ions having a drift time through the drift cell or ion mobility spectrometer of >5.25 ms. The two drift time or sampling windows preferably cover +/−10 standard deviations and therefore capture practically all of the ions.

In order to illustrate various aspects of the first embodiment the two ion populations may be considered to pass simultaneously through a drift cell or ion mobility spectrometer and the effect of imposing a first drift time window (Window 1) upon the two ion populations may be considered. According to an embodiment a non-destructive ion gate may be provided at the exit of the drift cell or ion mobility spectrometer or separator. The ion gate is preferably arranged to transmit ions (i.e. is switched OFF) during the first drift time or sampling window (Window 1) but is then arranged to block the onward transmission of ions (i.e. is switched ON) during the second drift time or sampling window after a delay time T1 as measured from the initial release of ions. As a result, during the second drift time or sampling window ions which arrive at the ion gate are preferably trapped within the drift cell or ion mobility spectrometer by the ion gate. Ions which are transmitted by the ion gate during the first drift time or sampling window are preferably trapped within an ion trap which is preferably arranged downstream of the ion gate.

As a result of imposing two drift time or sampling windows, ions falling within the first drift time or sampling window (i.e. those ions which are onwardly transmitted by the ion gate) will comprise 69.1% of the first ion population and 30.9% of the second ion population. These two ion populations are preferably retained in an ion trap arranged downstream of the drift cell or ion mobility spectrometer or separator.

The ions which are blocked by the ion gate (i.e. those ions having a drift time falling within the second drift time window) are preferably trapped within the drift cell or ion mobility spectrometer by the ion gate. These ions may then be passed back upstream through the drift cell or ion mobility spectrometer and are preferably stored within a first upstream ion trap.

The ions which are transmitted by the ion gate and which are trapped within the downstream ion trap may then be passed back upstream through the drift cell or ion mobility spectrometer and may then be trapped and stored within a second upstream ion trap. The second upstream ion trap is preferably arranged downstream of the first upstream ion trap.

Ions which have been transmitted by the ion gate and which are temporarily stored within the second Upstream ion trap may then be released from the second upstream ion trap and may then be passed back through the drift cell or ion mobility spectrometer or separator. According to this embodiment the ion gate remains OFF and the ions are preferably subjected to a conventional ion mobility scan wherein the drift time peaks of all the ions which are separated temporally as they pass through the drift cell or ion mobility spectrometer are determined.

Figure 2:
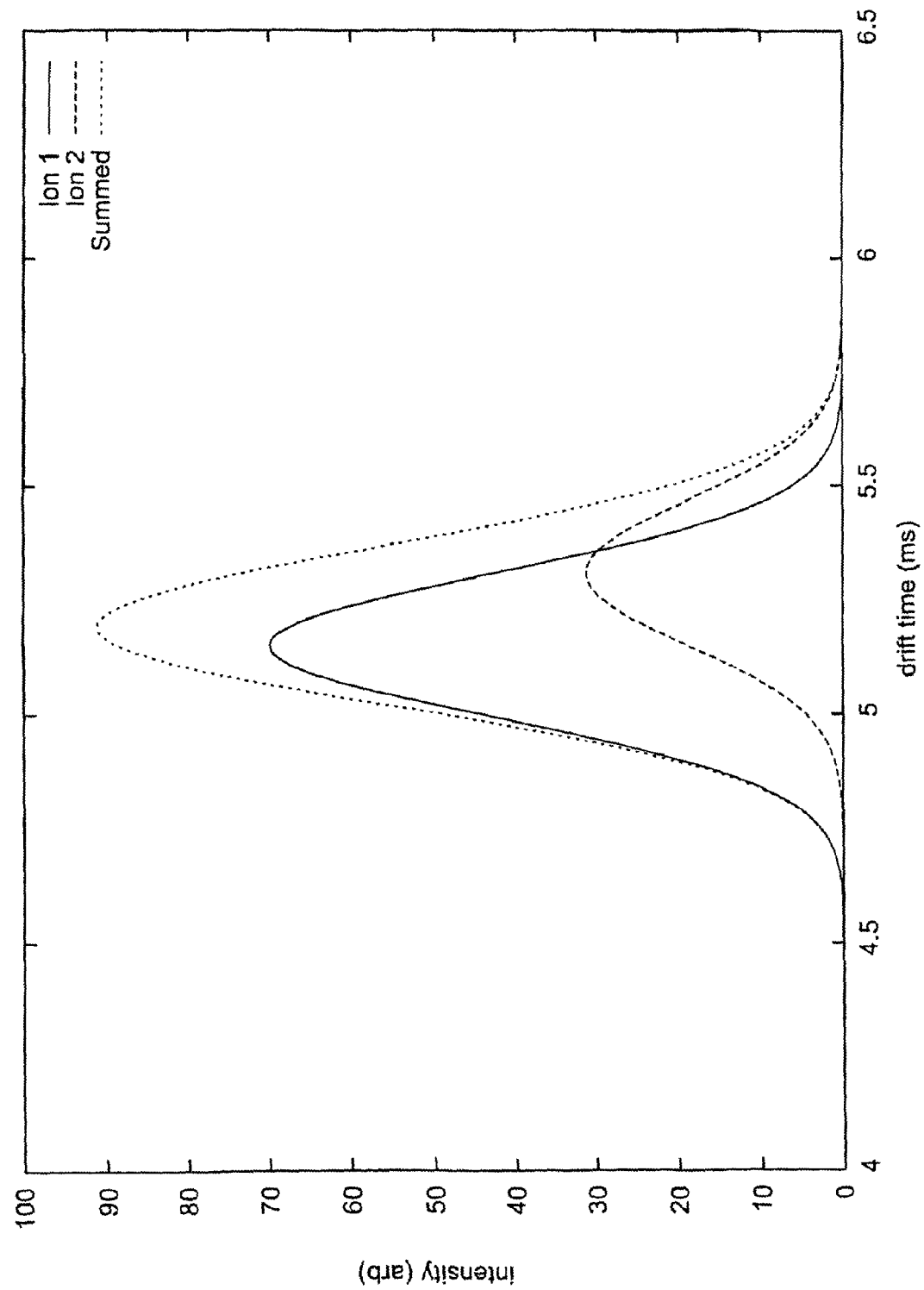
FIG. 2 shows drift time peaks after one sampling using a first time window according to a first embodiment of the present invention.

FIG. 2 shows the peak distributions of the two ion populations for those ions which were initially transmitted by the ion gate by the first drift time or sampling window and which were passed for a second time through the drift cell or ion mobility spectrometer or separator. The summed peak shows the ion peak which will actually be observed. It is noted that the observed mean drift time is now less than 5.25 ms and this is due to the ion population transmitted by the ion gate comprising a greater proportion of the first species of ions (which have a shorter average drift time than that of the second species of ions).

If instead of subjecting those ions which were previously transmitted by the ion gate to a conventional ion mobility scan, the ion gate is now switched ON again after the same delay time T1 then the ions released from the second upstream ion trap will then again be sampled using the same drift time or sampling window (Window 1). As a result, the ions which will emerge from the drift cell or ion mobility spectrometer after a second pass through the drift cell or ion mobility spectrometer or separator and sampling by the ion gate will comprise $0.69^2=47.8\%$ of the first ion population and $0.31^2=9.5\%$ of the second ion population.

According to various embodiments of the present invention this process may be repeated multiple times. For example, after four passes through the drift cell or ion mobility spectrometer or separator and samplings by the ion gate then the ion population which is transmitted by the ion gate will comprise $0.69^4=22.9\%$ of the first ion population and $0.31^4=0.9\%$ of the second ion population. The ratio of the first ion population R1 to the second ion population R2 will therefore be 22.9/0.9=25.4. It is apparent, therefore, that after four passes through the drift cell or ion mobility spectrometer or separator and corresponding ion gating events then the ions which emerge from the drift cell or ion mobility spectrometer will comprise approximately 25 times the population of the first ions relative to the second ions.

Figure 3A:
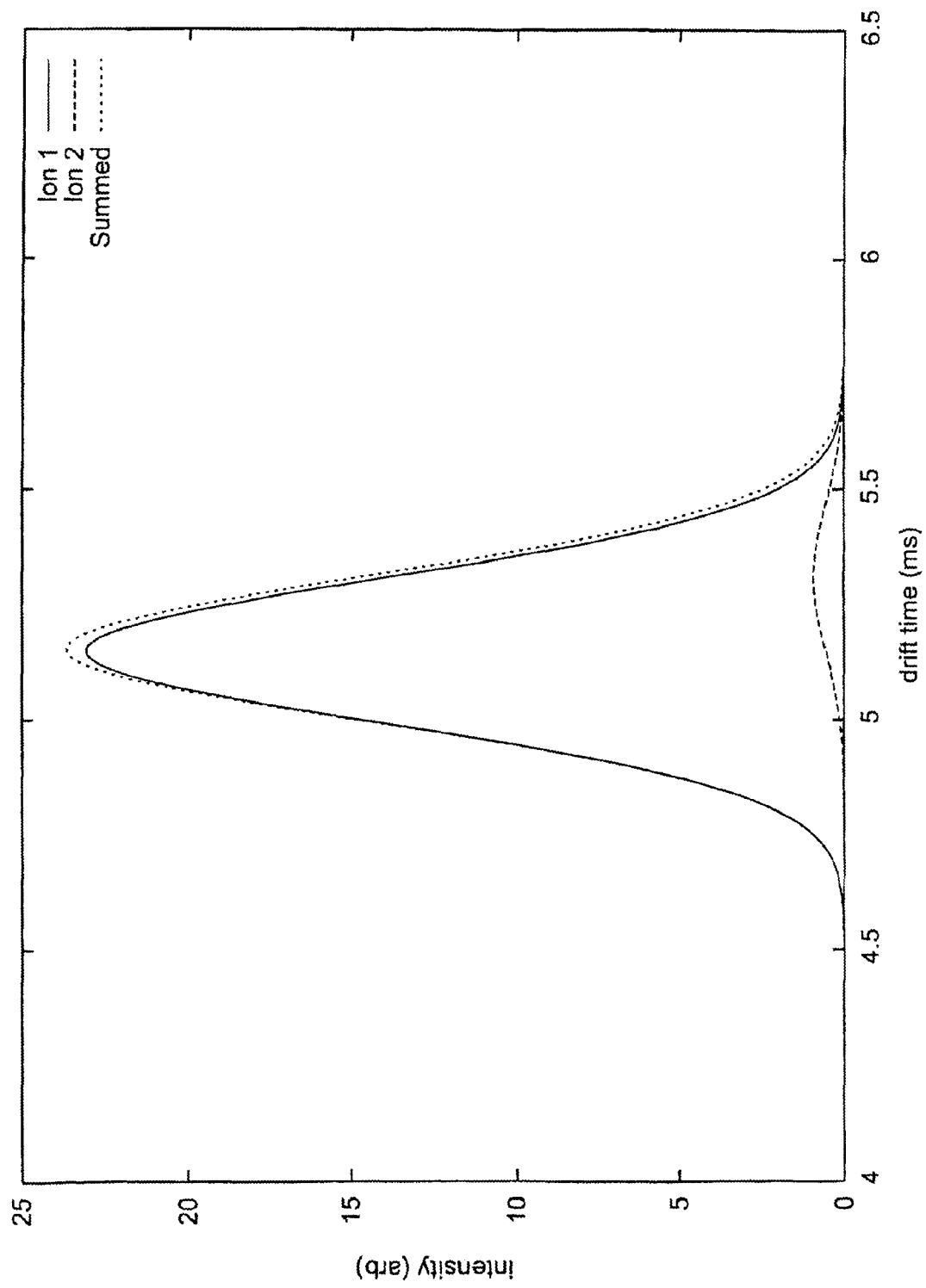
FIG. 3A shows drift time peaks after four samplings using a first time window according to a first embodiment of the present invention and FIG. 3B shows drift time peaks after four samplings using a second time window according to a first embodiment of the present invention wherein those ions which are sampled comprise ions retained from the process of sampling with a first time window.

FIG. 3A shows the ion populations after both ion populations have been passed four times through the drift cell or ion mobility spectrometer or separator and have been sampled by the first drift time window. In is apparent that the majority of the ions which are transmitted by the ion gate comprise the first species of ion.

As discussed above, according to the preferred embodiment those ions which are rejected by the first drift time or sampling window (i.e. those ions which fail to be transmitted by the non-destructive ion gate at any point in time) are preferably stored in a first upstream ion trap rather than being lost to the system. The ions which are stored after the ions have been sampled four times by the first drift time window will comprise 77.1% of the first ion population and 99.1% of the second ion population.

Those ions which are initially blocked by the ion gate and which are passed to the first upstream ion trap may then preferably be passed four times through the drift cell or ion mobility spectrometer whilst now sampling with the second drift time window (Window 2). According to this first embodiment only those ions which have drift times within the second drift time window (Window 2) are sampled. It is contemplated that those ions which emerge from the drift cell or ion mobility spectrometer during the first drift time window (window 1) are not retained in the downstream ion trap or less preferably may be removed by a destructive ion gate. Only those ions having drift times greater than 5.25 ms are preferably retained in the downstream ion trap. These ions are then passed back through the drift cell or ion mobility spectrometer to an upstream ion trap. If the ions are then passed four times through the drift cell or ion mobility spectrometer and are sampled by the second drift time window then the ion population which will ultimately emerge from the drift cell or ion mobility spectrometer will comprise $77.1*(0.31)^4=0.7\%$ of the first ion population and $99.1*(0.69)^4=22.5\%$ of the second ion population.

Figure 3B:
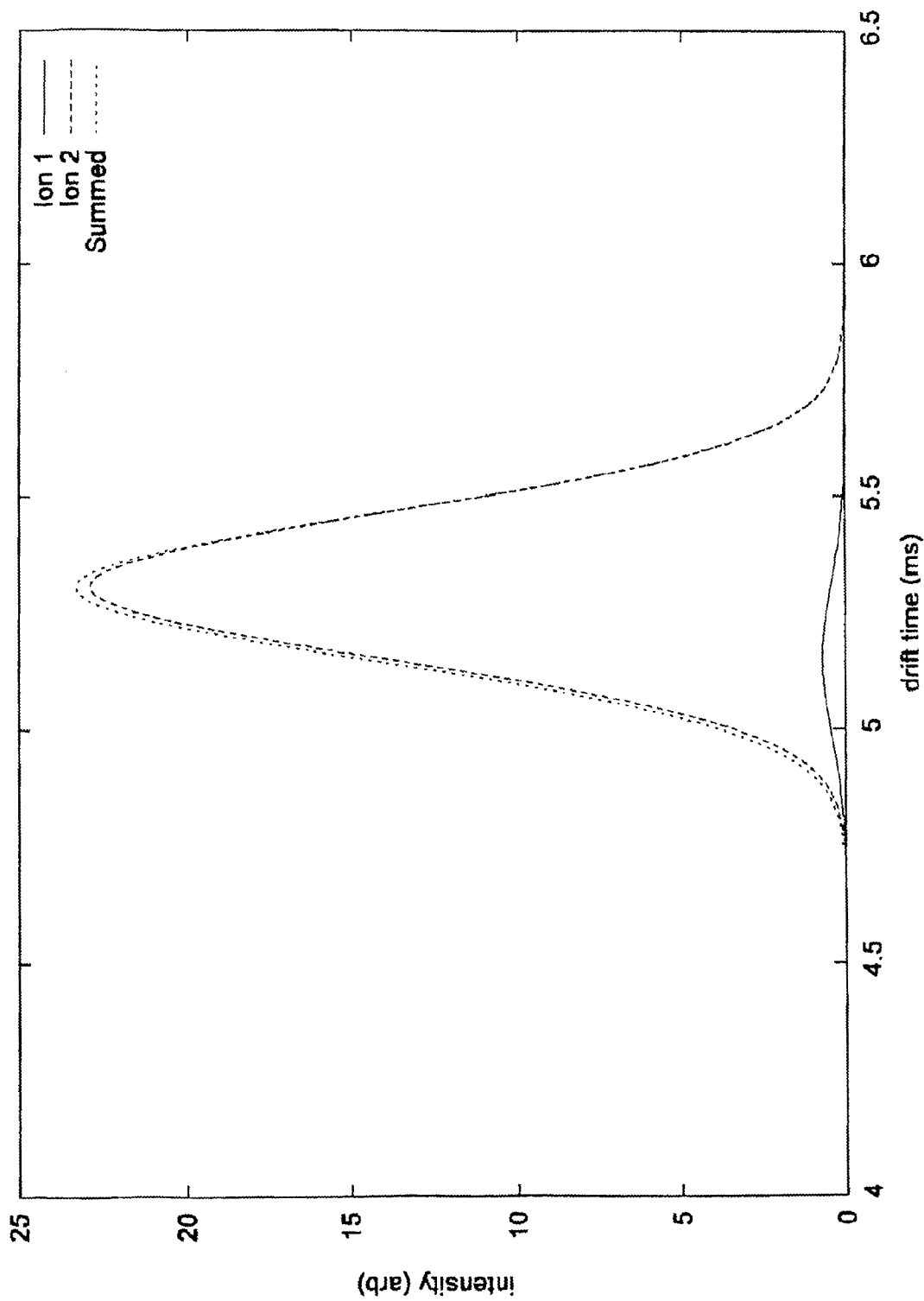

FIG. 3B shows the resulting drift time peaks after sampling those ions which remain after the first scan described above in relation to FIG. 3A four times using the second drift time or sampling window. It can be seen from FIG. 3B that the majority of the ions which emerge are the second species of ion.

It will be apparent that with reference to FIG. 1 that although the two species of ion are unresolved after a single pass through the drift cell or ion mobility spectrometer or separator nonetheless after four passes through the drift cell or ion mobility spectrometer or separator in the manner as described above with reference to FIGS. 3A and 3B then the two ion populations are essentially resolved.

According to the first embodiment ions which are passed through the drift cell or ion mobility spectrometer or separator are subjected to two fixed drift time or sampling windows.

Figure 4:
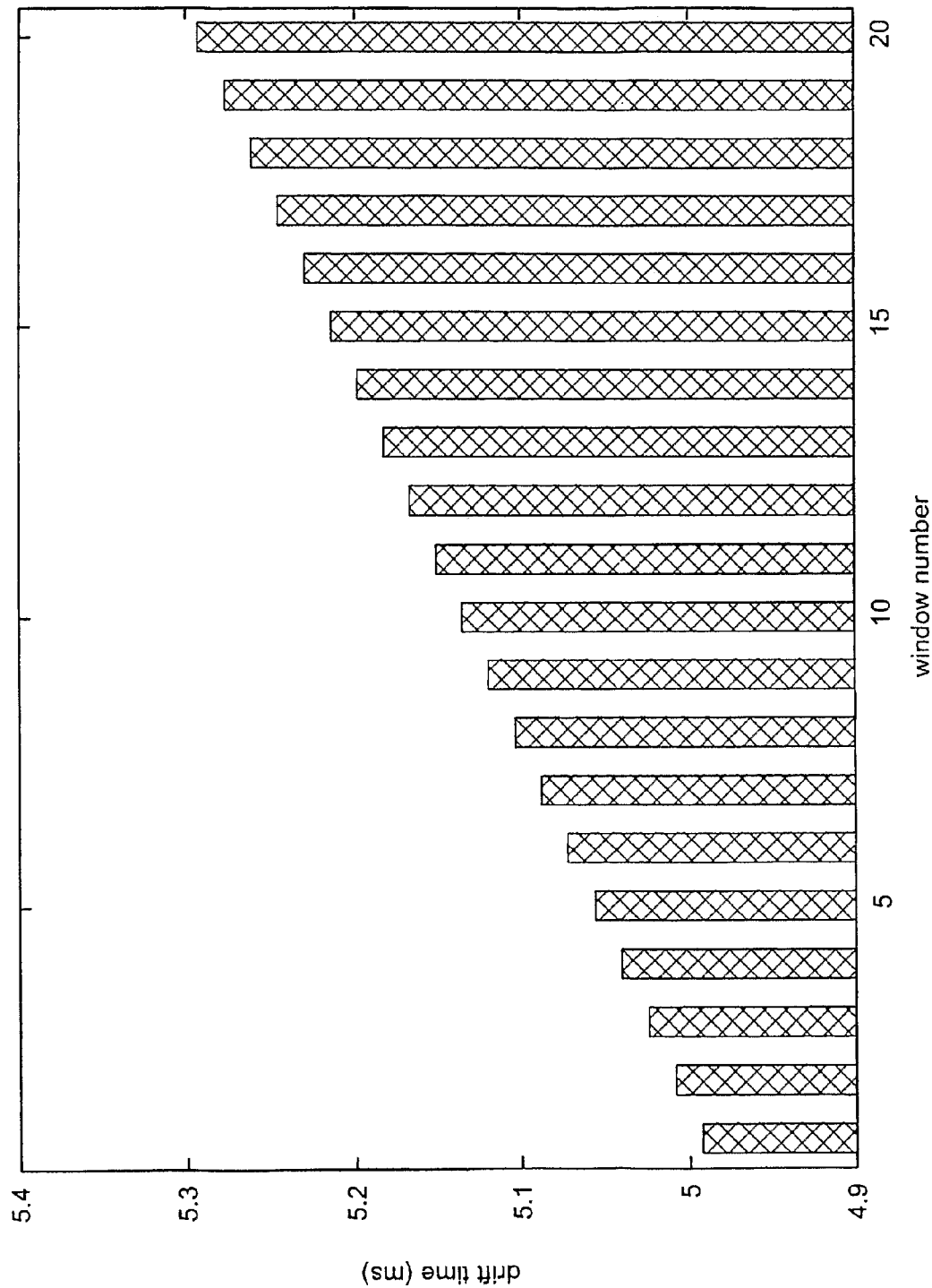
FIG. 4 shows a plot of successive drift time windows which may be used to sample ions according to a second embodiment of the present invention.

A second main embodiment of the present invention will now be described wherein drift time or sampling windows may be used or applied which progressively increase or vary with time. Each drift time or sampling window preferably comprises all drift times up to a specific drift time scan value. The scan value is preferably shifted or increased by an increment after n samplings have been performed so that the drift time window is preferably incrementally increased over the drift time scan region. FIG. 4 shows an example of how the drift time windows may increase during successive scans according to the second embodiment of the present invention.

According to the second embodiment ions are preferably subjected to n scans, passes or samplings through a drift cell or ion mobility spectrometer or Separator wherein the ions are sampled or gated each time by applying the same drift time or sampling window. Ions which are ungated are stored and are then subjected to n scans, passes or samplings through the drift cell or ion mobility spectrometer or separator wherein the ions are sampled or gated each by applying the same drift time or sampling window but which is slightly increased from the previous n scans. The second main embodiment corresponds to a scanning version of the first embodiment with the result that a plurality of drift time spectra (depending upon the scan region and increment) with varying proportions of the ion populations present in the spectra are obtained.

If the mean drift time position determined from the spectra is plotted versus the drift time scan point or maximum drift time transmitted by the ion gate then it is observed that for spectra which substantially correspond to a single ion population then the observed mean drift time remains essentially static since the contribution is solely from a single peak with a single mean drift time. However, as the contribution from a different ion population increases then the mean drift time of the spectra will begin to shift as it becomes comprised increasingly of a combination of different peaks. According to the second embodiment by plotting the mean observed drift time versus the drift time scan point or maximum drift time transmitted by the ion gate, regions can be determined by analysing the gradient of the curve wherein the ions principally comprise a single ion population.

Figure 5:
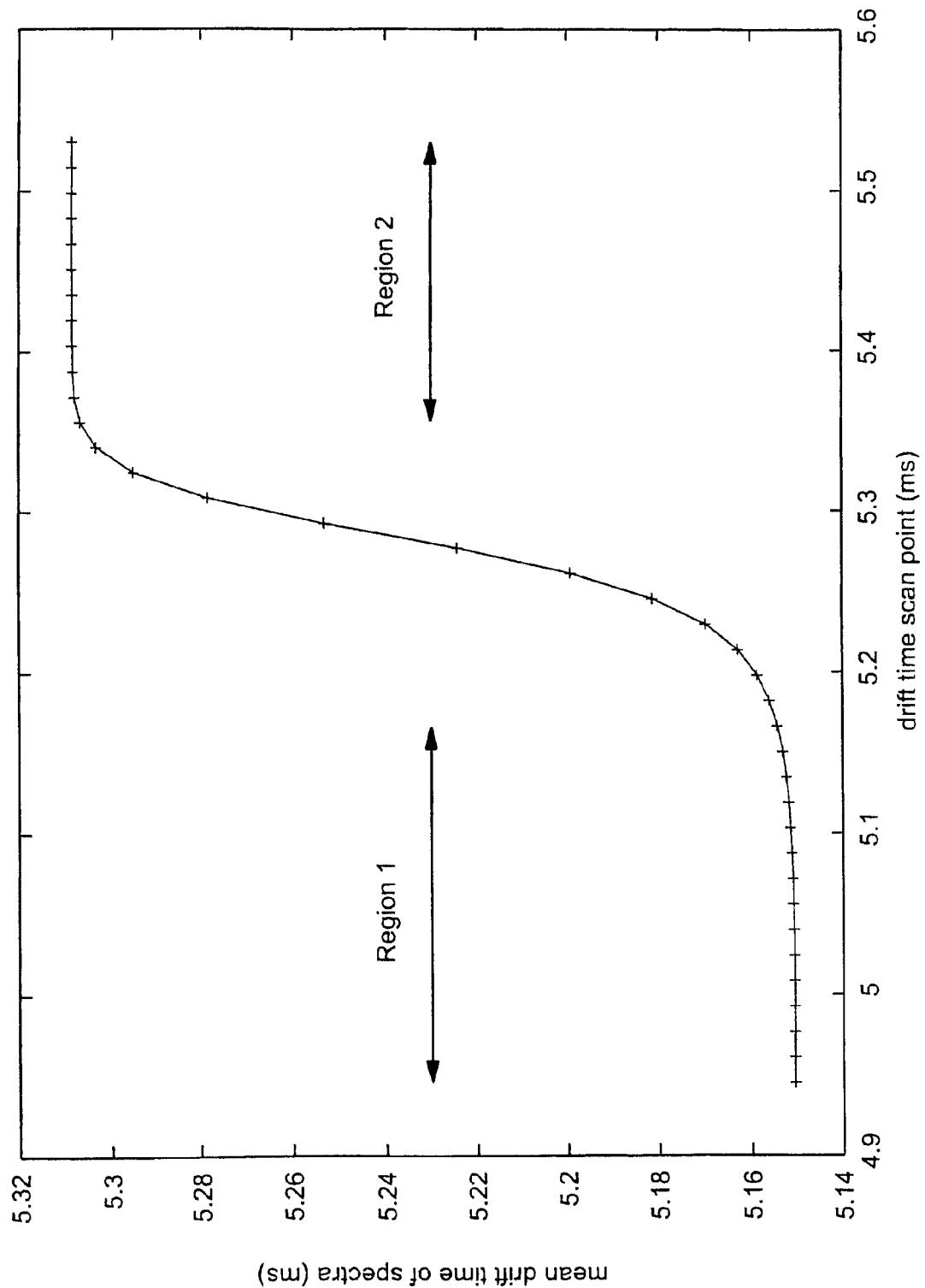
FIG. 5 shows a plot of mean drift time versus drift time scan point for the two ion populations as illustrated in FIG. 1 wherein regions corresponding to a single ion species are identified by limiting the gradient between successive points to be less than 0.1.

FIG. 5 shows the relationship between the mean observed drift time versus drift time scan point or maximum drift time transmitted by the ion gate for the two ion populations illustrated in FIG. 1 after four samplings at each window position and wherein the drift time window was increased by 0.0158 ms (0.1 of the peak standard deviation) after every four sampling at the same drift time window.

Spectra which contain principally a single ion population can be determined from the portions of this plot which have a low gradient. These spectra can then be summed together to obtain a resolved drift time peak which corresponds substantially with a single ion species.

Figure 6A:
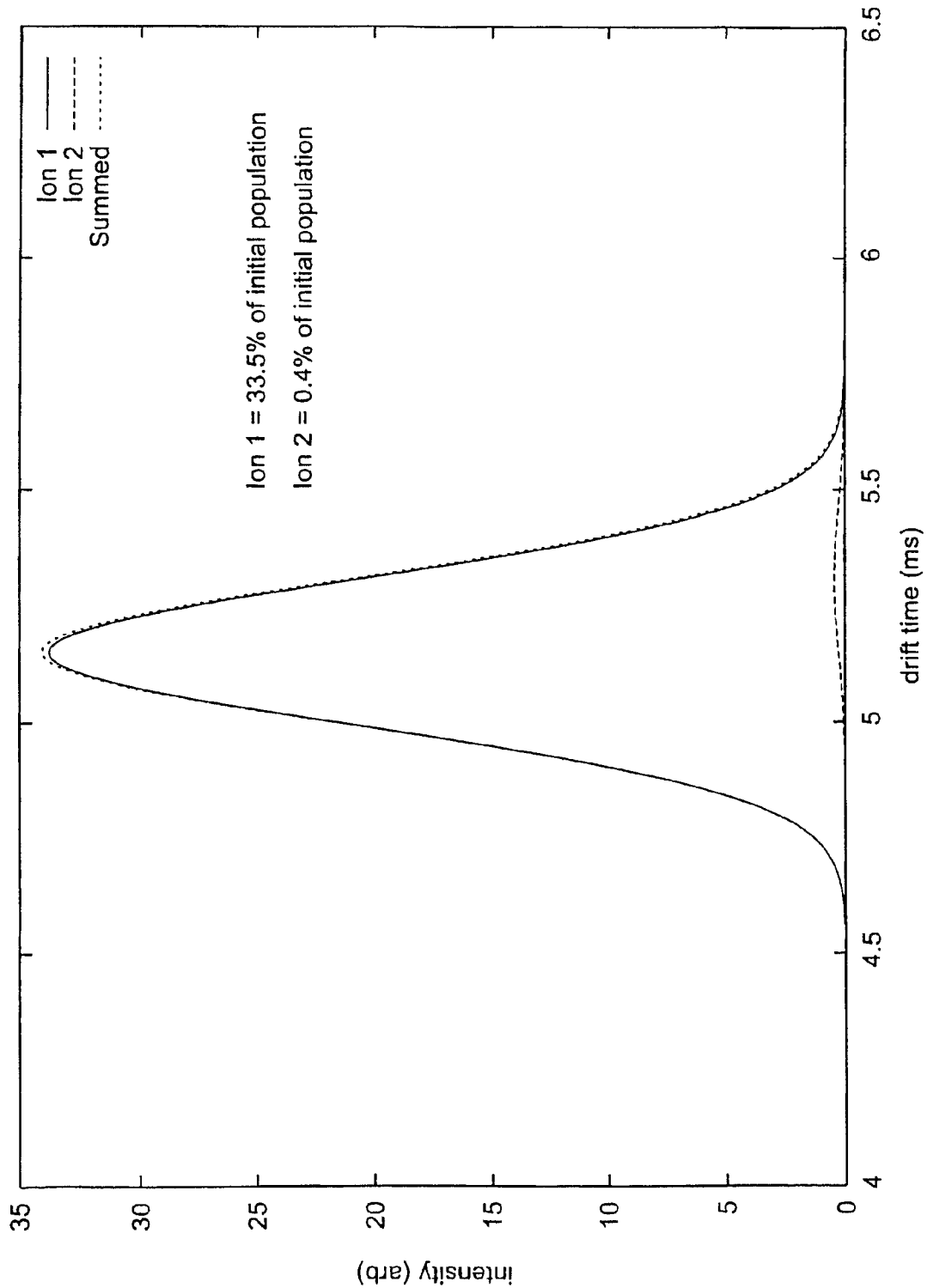
FIG. 6A shows individual and summed drift time spectra from the first region shown in FIG. 5 indicating that the ions substantially comprise the first ion species and FIG. 6B shows individual and summed drift time spectra from the second region shown in FIG. 5 indicating that the ions substantially comprise the second ion species.
Figure 6B:
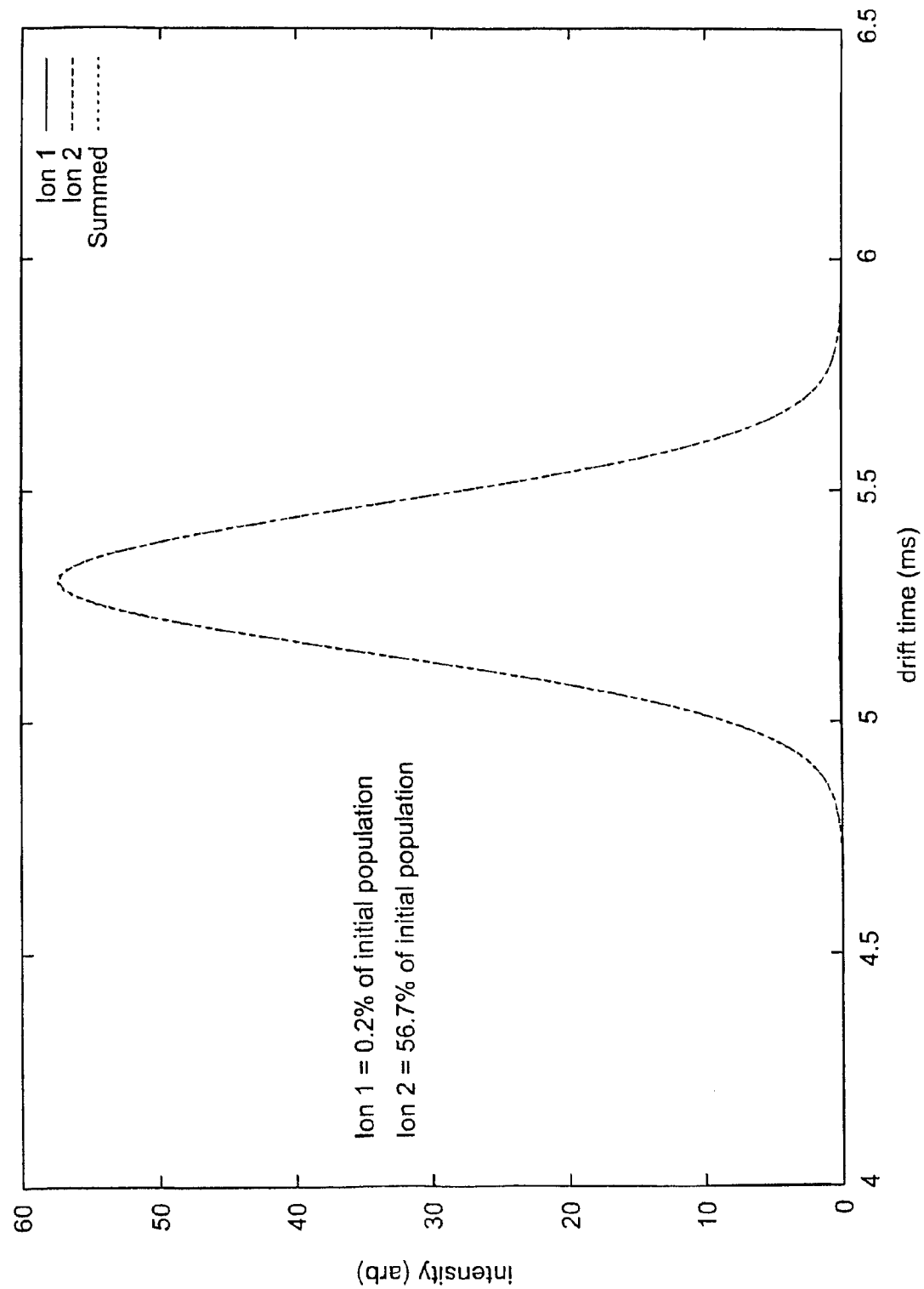

FIG. 6A shows the summed drift time spectra for drift time spectra indicated by region 1 in FIG. 5 and FIG. 6B shows the summed drift time spectra for drift time spectra indicated by region 2 in FIG. 5.

The drift time spectra of the summed region 1 as shown in FIG. 6A is such that the ions comprise 33.5% of the initial ion population of the first ion species and 0.4% of the initial ion population of the second ion species. The drift time spectra of the summed region 2 as shown in FIG. 6B is such that the ions comprise 0.2% of the initial ion population of the first ion species and 56.7% of the initial ion population of the second ion species.

It is apparent that according to the second embodiment the two ion peaks can be separated and a greater percentage of the resolved ions can be retained in the final summed drift time spectra compared with the approach of applying two fixed drift time windows according to the first embodiment. However, this is at the cost of a greater number of scan windows. For the embodiment shown in FIG. 5 thirty eight different scan windows are applied whereas according to the first embodiment only two scan windows are applied. Nonetheless, the second embodiment is particularly amenable to automated scanning whereas the first embodiment requires accurate initial positioning of the cut point between the two drift time windows. The second embodiment is also able to cope with separating more than two overlapping peaks as will now be discussed.

Figure 7:
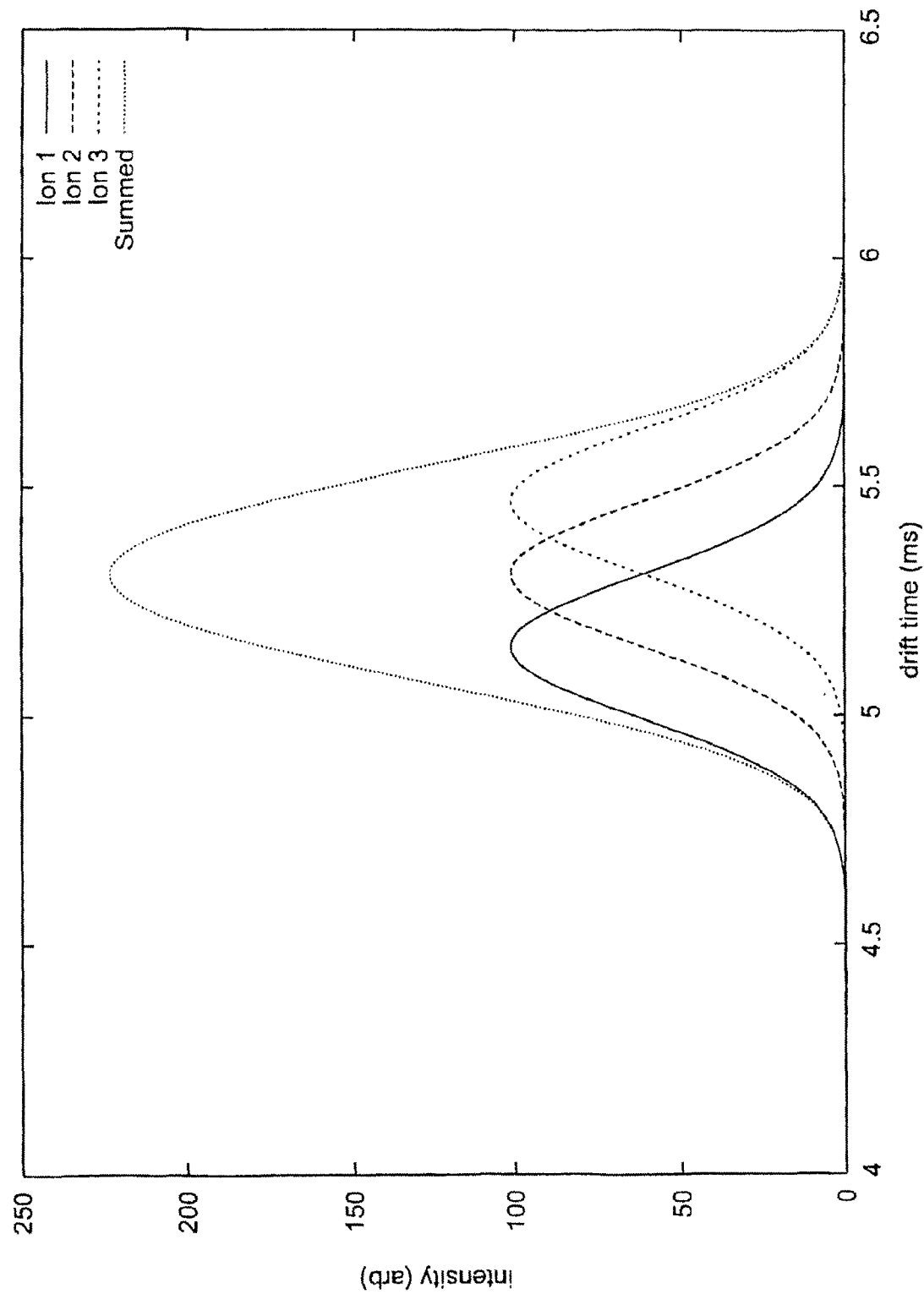
FIG. 7 shows individual and summed Gaussian drift time peaks for three ions having the same standard deviation wherein mean peaks are separated by one standard deviation.

FIG. 7 shows the individual and summed ion drift time peaks for three ions having the same peak standard deviation. The mean drift times are separated by one standard deviation between the first ion and the second ion, and likewise by one standard deviation between the second ion and the third ion.

FIG. 8 shows the mean drift time versus drift time scan point or maximum drift time transmitted by the ion gate for the three ion populations with four samplings at each window position and a drift time window increment of 0.0158 ms (0.1 of the peak standard deviation) as before. The three flat or relatively flat regions are selected or identified by limiting the gradient change between successive points to be 0.4.

FIG. 9A shows the final summed spectra for the first region (Region 1) shown in FIG. 8. The drift time spectra of the summed spectra for the first region (Region 1) as shown in FIG. 8 is such that the ions comprise 64.3% of the initial ion population of the first ion species, 2.2% of the initial ion population of the second ion species and 0.004% of the initial ion population of the third ion species.

FIG. 9B shows the final summed spectra for the second region (Region 2) shown in FIG. 8. The drift time spectra of the summed spectra for the second region (Region 2) as shown in FIG. 8 is such that the ions comprise 0.5% of the initial ion population of the first ion species, 30.7% of the initial ion population of the second ion species and 1.8% of the initial ion population of the third ion species.

FIG. 9C shows the final summed spectra for the third region (Region 3) shown in FIG. 8. The drift time spectra of the summed spectra for the third region (Region 3) as shown in FIG. 8 is such that the ions comprise virtually zero ($2 \times 10^{-9}$) of the initial ion population of the first ion species, 0.5% of the initial ion population of the second ion species and 66.4% of the initial ion population of the third ion species.

From these percentages it can be seen that the gain ratio of the desired ion population to the other ions is at least 30/15/130 for the three ion regions respectively.

A third embodiment is contemplated for separating two peaks having the same mean drift time but having differing standard deviations. FIG. 10 shows the initial ion populations for such a case. From this plot it can be seen that by sampling the left hand edge of the broader peak it is possible to build up a population with a significant bias towards the ions in the broader distribution. Sampling of a narrow window in the centre of the peak will enable a population biased towards the narrower peak to be obtained. The shifting mean drift time method, however, cannot be used to estimate the relative contributions of a sampled spectrum since the mean drift times are identical. However, the peaks can be analysed based on the change in standard deviation. A limitation of this approach is that it requires two ions having identical mass to charge ratios and identical ion mobilities but having different standard deviations. Differing charge states can have the same mass to charge ratio and different standard deviations but are unlikely to also have the same ion mobility.

FIG. 11 illustrates a preferred embodiment of the present invention wherein an ion source 1 is provided upstream of a mass filter 2 which preferably comprises a quadrupole rod set mass filter. A first upstream ion trap 3 and a second upstream ion trap 4 are preferably provided upstream of a drift cell or ion mobility spectrometer or separator 5. A non-destructive ion gate or shutter 6 is preferably provided downstream of the drift cell or ion mobility separator 5. A downstream ion trap 7 is preferably provided downstream of the ion gate 6 and an ion detector 8 is preferably provided downstream of the downstream ion trap 7. The ion detector 8 may comprise a point detector, a Time of Flight mass analyser, a quadrupole rod set mass analyser or a Fourier Transform mass spectrometer. Other embodiments are contemplated wherein the ion detector 8 may comprise alternative forms of ion detector.

According to a preferred embodiment the drift cell or ion mobility spectrometer or separator 5 preferably comprises a travelling wave ion mobility spectrometer or separator drift cell 5. Ions with a given mobility will pass through the ion mobility spectrometer or separator 5 and will exit with a drift time distribution that is approximately Gaussian and having a mean and standard deviation that is related to the mobility of the ion, the gas pressure in the drift cell and the travelling wave pulse.

The ion gate 6 is preferably arranged at the exit of the ion mobility spectrometer or separator cell 5 and is preferably arranged to only allow transmission of ions up to a selected drift time $T_g$. Ions which are onwardly transmitted are stored in the downstream ion trap 7 whilst the remaining rejected ions are returned to the first upstream ion trap 3. The population of ions (R1 for ion 1, R2 for ion 2 etc.) in the downstream ion trap 7 will be given by the overlap of the various Gaussian drift time distributions of the ions and the selected drift time window. The ratio of two ion populations in the downstream ion trap 7 is therefore given by R1/R2.

The population of ions in the downstream ion trap 7 is preferably transported back through the ion mobility spectrometer or separator cell 5 to the second upstream ion trap 4 where the ions are essentially renormalized (i.e. no drift time separation is retained). The ion population is then preferably rescanned with the same gating event occurring. Rejected ions are returned back through the drift cell or ion mobility spectrometer or separator and are stored in the first upstream ion trap 3. The new population of ions in the downstream ion trap 7 is given by $(R1/R2)^2$. This sequence may be repeated a number of times. A final pass through the ion mobility spectrometer or separator 5 is preferably performed with no gating event (i.e. a conventional ion mobility scan is performed), resulting in the drift time peak profiles of the final ion populations $(R1/R2)^n$. According to the second embodiment the drift time gate $T_g$ is then preferably incremented and the rejected ions from the n scans stored in the first upstream ion trap 3 are now preferably used as the initial population for a new scan. This sequence of operation will be discussed in more detail below with reference to FIGS. 12-19.

FIG. 12 shows an aspect of an embodiment of the present invention wherein ions are generated by an ion source 1. Ions having a particular mass or mass to charge ratio are onwardly transmitted by the mass filter 2 whereas ions having undesired masses or mass to charge ratios are attenuated by the mass filter 2. Ions having a particular or desired ion population are stored in a first upstream ion trap 3.

FIG. 13 shows an aspect of an embodiment of the present invention wherein the ion source 1 is now switched OFF so that no more ions are generated for the time being. Ions which have been stored in the first upstream ion trap 3 whilst the ion source 1 was switched ON are now preferably moved from the first upstream ion trap 3 to the second upstream ion trap 4.

FIG. 14 shows a further aspect of an embodiment of the present invention wherein ions are now ejected from the second upstream ion trap 4 and are preferably passed to the drift cell or ion mobility separator 5 which is arranged to separate ions temporally according to their ion mobility. The non-destructive ion gate 6 is preferably arranged initially to be open (i.e. switched OFF) when ions are initially released from the second upstream ion trap 4. The ion gate is arranged to be closed (i.e. to be switched ON) after a time Tg from when ions are initially been released from the second upstream ion trap 4. Those ions which have already passed through the ion gate 6 by the time that the ion gate 6 is closed at time $T_g$ are trapped in the downstream ion trap 7. Ions which have not passed the ion gate 6 by time $T_g$ are temporarily trapped within the ion mobility separator 5 by the ion gate 6.

FIG. 15 shows an aspect of an embodiment wherein those ions which have not passed the ion gate 6 by time $T_g$ and which are have therefore become trapped within the ion mobility separator 5 by the ion gate 6 are now passed back upstream through the ion mobility separator 5. The ions are preferably also transmitted through the second upstream ion trap 4 so that the ions preferably become trapped in the first upstream ion trap 3. In this mode of operation when the ions are passed back upstream through the ion mobility separator 5, the ion mobility separator 5 is preferably operated in an ion guide only mode of operation i.e. ions are not separated according to their ion mobility as they are passed back upstream.

FIG. 16 shows a further aspect of an embodiment of the present invention wherein those ions which passed through the ion gate 6 before the ion gate 6 was closed at time $T_g$ and which were temporarily trapped in the downstream ion trap 7 are now sent back upstream through the ion mobility separator 5. The ions are preferably stored in the second upstream ion trap 4. In this mode of operation when ions are passed back upstream through the ion mobility separator 5, the ion mobility separator 5 is preferably operated in an ion guide only of operation i.e. ions are not separated according to their ion mobility as they are passed back upstream.

FIG. 17 shows an aspect of an embodiment of the present invention wherein those ions which are initially transmitted by the ion gate 6 and which were sent back upstream to be stored in the second upstream ion 4 are now passed back through the ion mobility separator 5. The ions are temporally separated as they pass through the ion mobility separator 5 and the ion gate 6 preferably remains OFF as ions emerge from the ion mobility separator 5. The ions which emerge from the ion mobility separator 5 are then preferably detected by the ion detector 8.

FIG. 18 illustrates how ions are released from a second upstream ion trap 4 at an initial time T=0 and the ion gate 6 is then arranged to block the onward transmission of ions (i.e. is switched ON) at a subsequent time $T=T_g$. FIG. 18 also shows how the delay time between the release of ions from the upstream ion trap 4 to the switching ON of the ion gate 6 is preferably increased with time according to the second embodiment of the present invention.

FIG. 19 shows a flow diagram illustrating a preferred mode of operation. Ions are initially generated and stored in a first upstream ion trap 3 according to a first mode of operation (referred to as "state 1" in FIG. 19) and as shown and described with relation to FIG. 12. The ions are then preferably transferred from the first upstream ion trap 3 to the second upstream ion trap 4 in a second mode of operation (referred to as "state 2" in FIG. 19) and as shown and described with relation to FIG. 13. The desired number of passes n through the drift cell or ion mobility spectrometer or separator 5 is then preferably set. The ions are then preferably passed from the second upstream ion trap 4 into the drift cell or ion mobility spectrometer 5 so that the ions become separated temporally according to their ion mobility in a third mode of operation (referred to as "state 3" in FIG. 19) and as shown and described with relation to FIG. 14. The non-destructive ion gate 6 is preferably shut after a time $T_g$ from the release of ions from the second upstream ion trap 4. Ions which are trapped within the drift cell or ion mobility spectrometer 5 are then preferably passed upstream and are trapped in the first upstream ion trap 3 in a fourth mode of operation (referred to as "state 4" in FIG. 19) and as shown and described with relation to FIG. 15.

Ions transmitted by the ion gate 6 and which are trapped within the downstream ion trap 7 are then passed back upstream and are trapped in the second upstream ion trap 4 in a fifth mode of operation (referred to as "state 5" in FIG. 19) and as shown and described with relation to FIG. 16. The value n is then reduced by one to reflect that ions have been passed through the ion mobility spectrometer or separator 5 and gated by the ion gate 6. If the value n is reduced to zero then the mass spectrometer then proceeds to a sixth mode of operation (referred to as "state 6" in FIG. 19) and as shown and described with relation to FIG. 17 wherein ions from the second upstream ion trap 4 are passed through the ion mobility spectrometer or separator whilst the ion gate 6 remains OFF (so that a conventional ion mobility scan is performed) and the ions are then detected by the ion detector 8 and are mass analysed. Otherwise, if n>1 then the mass spectrometer repeats the process as indicated by the third mode of operation shown and described above in relation to FIG. 14 of passing the ions back through the ion mobility spectrometer or separator 5, separating the ions according to their ion mobility and shutting the ion gate 6 after a time $T_g$.

Once the process of gating ions multiple times after a certain delay time $T_g$ has been completed, those ions which did not pass through the ion gate 6 at any stage and which were transferred to the first upstream ion trap 3 are then passed from the first upstream ion trap 3 to the second upstream ion trap 4 as shown in the second mode of operation in FIG. 13. The period of time $T_g$ between the release of ions from the second upstream ion trap 4 to the application of a gate voltage on the non-destructive ion gate 6 is then increased and the process of passing ions through the ion mobility spectrometer or separator 5 and switching the ion gate 6 ON after a delay time is repeated. The various cycles of operation described above preferably continue until the delay time reaches a maximum delay time $T_{gmax}$. At this point, the mass spectrometer preferably reverts to the first mode of operation as shown and described above in relation to FIG. 12 wherein a new group of ions is generated by the ion source 1. The ions are then preferably mass filtered by the mass filter 2 so that a new population of ions is then stored in the first upstream ion trap 3. The process is then preferably repeated.

Although the present invention has been described with reference to preferred embodiments, it will be understood by those skilled in the art that various modifications in form and detail may be made to the particular embodiments discussed above without departing from the scope of the present invention as set forth in the accompanying claims.

The invention claimed is:

1. A method of mass spectrometry comprising:
passing a first group of ions through an ion mobility spectrometer or separator in order to separate temporally at least some of said ions;
operating an ion gate so that ions having drift times within a time window T1 are transmitted by said ion gate but ions having drift times outside of said time window T1 are not transmitted by said ion gate;
passing at least some of said ions having drift times within said time window T1 through said ion mobility spectrometer or separator again in order to separate temporally at least some of said ions; and
passing at least some or substantially all of said ions having drift times outside of said time window T1 back through said ion mobility spectrometer or separator and storing said ions in a first upstream ion trap; wherein
prior to passing at least some of said ions having drift times within said time window T1 through said ion mobility spectrometer or separator again said method further comprises the steps of:
trapping said ions having drift times within said time window T1 in a downstream ion trap, passing said ions back upstream through said ion mobility spectrometer or separator, storing said ions in a second upstream ion trap and ejecting said ions from said second upstream ion trap into said ion mobility spectrometer or separator.

2. A method as claimed in claim 1, further comprising:
operating said ion gate so that ions having drift times within a time window T2 are transmitted by said ion gate but ions having drift times outside of said time window T2 are not transmitted by said ion gate;
passing at least some or substantially all of said ions having drift times outside of said time window T2 back through said ion mobility spectrometer or separator and storing said ions in a first upstream ion trap; and
trapping said ions having drift times within said time window T2 in a downstream ion trap, passing said ions back upstream through said ion mobility spectrometer or separator, storing said ions in a second upstream ion trap, ejecting said ions from said second upstream ion trap into said ion mobility spectrometer or separator and passing at least some of said ions having drift times within said time window T2 through said ion mobility spectrometer or separator again in order to separate temporally at least some of said ions.

3. A method as claimed in claim 1, further comprising:
operating said ion gate so that ions having drift times within a time window T3 are transmitted by said ion gate but ions having drift times outside of said time window T3 are not transmitted by said ion gate;
passing at least some or substantially all of said ions having drift times outside of said time window T3 back through said ion mobility spectrometer or separator and storing said ions in a first upstream ion trap;
trapping said ions having drift times within said time window T3 in a downstream ion trap, passing said ions back upstream through said ion mobility spectrometer or separator, storing said ions in a second upstream ion trap, ejecting said ions from said second upstream ion trap into said ion mobility spectrometer or separator and passing at least some of said ions having drift times within said time window T3 through said ion mobility spectrometer or separator again in order to separate temporally at least some of said ions; and optionally mass analysing at least some of said ions which emerge from said ion mobility spectrometer or separator.

4. A method as claimed in claim 2, wherein said first time window T1 or said second time window T2 or said third time window T3 are substantially the same or substantially different.

5. A method as claimed in claim 1, further comprising:
ejecting at least some of said ions having drift times outside of said time windows T1, T2 and T3 from said first upstream ion trap into said ion mobility spectrometer or separator as a second group of ions.

6. A method as claimed in claim 5, further comprising:
passing said second group of ions through said ion mobility spectrometer or separator in order to separate temporally at least some of said ions;
operating an ion gate so that ions having drift times within a time window T4 are transmitted by said ion gate but ions having drift times outside of said time window T4 are not transmitted by said ion gate;
passing at least some of said ions having drift times within said time window T4 through said ion mobility spectrometer or separator again in order to separate temporally at least some of said ions; and optionally
passing at least some or substantially all of said ions having drift times outside of said time window T4 back through said ion mobility spectrometer or separator and storing said ions in a first upstream ion trap.

7. A method as claimed in claim 6, wherein prior to passing at least some of said ions having drift times within said time window T4 through said ion mobility spectrometer or separator again said method further comprises the steps of:
trapping said ions having drift times within said time window T4 in a downstream ion trap, passing said ions back upstream through said ion mobility spectrometer or separator, storing said ions in a second upstream ion trap and ejecting said ions from said second upstream ion trap into said ion mobility spectrometer or separator.

8. A method as claimed in claim 6, further comprising:
operating said ion gate so that ions having drift times within a time window T5 are transmitted by said ion gate but ions having drift times outside of said time window T5 are not transmitted by said ion gate;
passing at least some or substantially all of said ions having drift times outside of said time window T5 back through said ion mobility spectrometer or separator and storing said ions in a first upstream ion trap; and
trapping said ions having drift times within said time window T5 in a downstream ion trap, passing said ions back upstream through said ion mobility spectrometer or separator, storing said ions in a second upstream ion trap, ejecting said ions from said second upstream ion trap into said ion mobility spectrometer or separator and passing at least some of said ions having drift times within said time window T5 through said ion mobility spectrometer or separator again in order to separate temporally at least some of said ions.

9. A method as claimed in claim 6, further comprising:
operating said ion gate so that ions having drift times within a time window T6 are transmitted by said ion gate but ions having drift times outside of said time window T6 are not transmitted by said ion gate;
passing at least some or substantially all of said ions having drift times outside of said time window T6 back through said ion mobility spectrometer or separator and storing said ions in a first upstream ion trap;
trapping said ions having drift times within said time window T6 in a downstream ion trap, passing said ions back upstream through said ion mobility spectrometer or separator, storing said ions in a second upstream ion trap, ejecting said ions from said second upstream ion trap into said ion mobility spectrometer or separator and passing at least some of said ions having drift times within said time window T6 through said ion mobility spectrometer or separator again in order to separate temporally at least some of said ions; and optionally
mass analysing at least some of said ions which emerge from said ion mobility spectrometer or separator.

10. A method as claimed in claims 6, wherein either:
(i) said time window T4 and said time window T5 and said time window T6 are substantially the same; or
(ii) said time window T4 and said time window T5 and said time window T6 are substantially different.

11. A method as claimed in claims 6, wherein either:
(i) said time window T4 and said time window T5 and said time window T6 are substantially different to said time window T1 and said time window T2 and said time window T3; or
(ii) said time window T4 and said time window T5 and said time window T6 are substantially the same as said time window T1 and said time window T2 and said time window T3.

12. A method as claimed in claim 1, further comprising obtaining an ion mobility spectrum corresponding substantially to a single ion species by:
determining the mean drift time of ions through said ion mobility spectrometer or separator as a function of the maximum drift time of ions transmitted by said ion gate;
determining at least one time period during which said mean drift time remains substantially constant as a function of the maximum drift time of ions transmitted by said ion gate; and
forming a composite ion mobility spectrum by summing ion mobility data obtained during said time period.

13. A method as claimed in claim 1, wherein said ions having drift times within said time window T1 or said time window T2 or said time window T3 or said time window T4 or said time window T5 or said time window T6 are not substantially fragmented when entering and whilst being stored in said downstream ion trap or when entering and whilst being stored in said second upstream ion trap.

14. A method as claimed in claim 1, wherein said ions having drift times outside said time window T1 or outside said time window T2 or outside said time window T3 or outside said time window T4 or outside said time window T5 or outside said time window T6 are not substantially fragmented when entering and whilst being stored in said first upstream ion trap.

15. A mass spectrometer comprising:
an ion mobility spectrometer or separator;
an ion gate arranged downstream of said ion mobility spectrometer or separator; and
a first ion trap arranged upstream of said ion mobility spectrometer or separator;
a second ion trap arranged upstream of said ion mobility spectrometer or separator;
a third ion trap arranged downstream of said ion mobility spectrometer or separator; and
a control system arranged and adapted:
(i) to cause a first group of ions to pass through said ion mobility spectrometer or separator in order to separate temporally at least some ions;

(ii) to operate said ion gate so that ions having drift times within a time window T1 are transmitted by said ion gate but ions having drift times outside of said time window T1 are not transmitted by said ion gate;

(iii) to cause at least some of said ions having drift times within said time window T1 to pass through said ion mobility spectrometer or separator again in order to separate temporally at least some of said ions; and (iv) to cause at least some or substantially all of said ions having drift times outside of said time window T1 to pass back through said ion mobility spectrometer or separator and storing said ions in said first ion trap; wherein prior to passing at least some of said ions having drift times within said time window T1 through said ion mobility spectrometer or separator again said control system is arranged and adapted:

(v) to trap said ions having drift times within said time window T1 in said third ion trap, to pass said ions back upstream through said ion mobility spectrometer or separator, to store said ions in said second ion trap and elect said ions from said second ion trap into said ion mobility spectrometer or separator.

* * * * *